United States Patent
Weisman et al.

(10) Patent No.: US 10,780,001 B2
(45) Date of Patent: Sep. 22, 2020

(54) METHOD OF MAXIMIZING SHIPPING EFFICIENCY OF ABSORBENT ARTICLES

(71) Applicant: The Procter & Gamble Company, Cincinnati, OH (US)

(72) Inventors: Paul Thomas Weisman, Cincinnati, OH (US); Dean Larry Duval, Lebanon, OH (US); Harald Hermann Hundorf, Bonnn (DE); Holger Beruda, Schwalbach (DE); Horst Blessing, Cincinnati, OH (US); Peter Dziezok, Hochheim (DE); Axel Krause, Erfstadt (DE); Mattias Schmidt, Idstein (DE); Lutz Stelzig, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 1901 days.

(21) Appl. No.: 14/163,055

(22) Filed: Jan. 24, 2014

(65) Prior Publication Data
US 2014/0143180 A1    May 22, 2014

Related U.S. Application Data

(63) Continuation of application No. 12/890,800, filed on Sep. 27, 2010, now Pat. No. 8,676,549.
(Continued)

(51) Int. Cl.
*B65D 85/07* (2017.01)
*A61F 13/551* (2006.01)
(Continued)

(52) U.S. Cl.
CPC .... *A61F 13/55115* (2013.01); *A61F 13/5511* (2013.01); *B65D 71/0096* (2013.01);
(Continued)

(58) Field of Classification Search
CPC .. B65D 21/08; B65D 2581/055; B65D 81/02; B65D 81/107; B65D 81/113; A61F 2310/00371
(Continued)

(56) References Cited

U.S. PATENT DOCUMENTS 3,645,060 A   2/1972   Hammond
3,860,003 A   1/1975   Buell
(Continued)

FOREIGN PATENT DOCUMENTS

CA   1057373   6/1979
CA   2678090   12/2009
(Continued)

OTHER PUBLICATIONS

International Search Report, PCT/US2010/050609, dated Mar. 9, 2011, 13 pages.
(Continued)

*Primary Examiner* — King M Chu
(74) *Attorney, Agent, or Firm* — Charles R. Matson; Richard L. Alexander

(57) ABSTRACT

A process for shipping absorbent products having a substantially airfelt free absorbent core, on pallets, is provided. The loaded pallet comprises a plurality of packages, each having a plurality of disposable absorbent articles disposed within the interior space of the package, wherein the plurality of packages are arranged on the pallet such that the plurality of packages on the pallet exhibit a density of from about 11.0 lbs/ft$^3$ to about 14.6 lbs/ft$^3$.

25 Claims, 17 Drawing Sheets

Related U.S. Application Data

(60) Provisional application No. 61/246,690, filed on Sep. 29, 2009.

(51) Int. Cl.
*B65D 71/00* (2006.01)
*G06Q 90/00* (2006.01)
*A61F 13/53* (2006.01)

(52) U.S. Cl.
CPC ............. *B65D 85/07* (2018.01); *G06Q 90/00* (2013.01); *A61F 2013/5307* (2013.01)

(58) Field of Classification Search
USPC .......................... 206/433; 604/366, 367, 389
See application file for complete search history.

(56) References Cited

U.S. PATENT DOCUMENTS

| | | | |
|---|---|---|---|
| 4,610,678 A | 9/1986 | Weisman et al. | |
| 4,834,735 A | 5/1989 | Alemany et al. | |
| 4,888,231 A | 12/1989 | Angstadt | |
| 4,940,464 A | 7/1990 | Van Gompel et al. | |
| 5,037,416 A | 8/1991 | Allen et al. | |
| 5,092,861 A | 3/1992 | Nomura et al. | |
| 5,151,092 A | 9/1992 | Buell et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,387,207 A | 2/1995 | Dyer et al. | |
| 5,397,316 A | 3/1995 | LaVon et al. | |
| 5,460,622 A | 10/1995 | Dragoo et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,625,222 A | 4/1997 | DesMarais et al. | |
| 5,749,783 A | 5/1998 | Pollklas | |
| 5,897,545 A | 4/1999 | Kline et al. | |
| 5,934,470 A | 8/1999 | Bauer et al. | |
| 5,957,908 A | 9/1999 | Kline et al. | |
| 6,004,306 A | 12/1999 | Robles et al. | |
| 6,120,487 A | 9/2000 | Ashton | |
| 6,120,489 A | 9/2000 | Johnson et al. | |
| 6,229,061 B1 | 5/2001 | Dragoo et al. | |
| 7,750,203 B2 | 7/2010 | Becker et al. | |
| 8,169,305 B2 | 5/2012 | Matsumoto et al. | |
| 8,496,637 B2 | 7/2013 | Hundorf et al. | |
| 8,585,666 B2 | 11/2013 | Weisman et al. | |
| 8,676,549 B2 | 3/2014 | Weisman et al. | |
| 9,173,785 B2 | 11/2015 | Weisman et al. | |
| 10,123,916 B2 | 11/2018 | Weisman et al. | |
| 2002/0087371 A1 | 7/2002 | Abendroth | |
| 2003/0163292 A1 | 8/2003 | Eckenwiler et al. | |
| 2003/0233082 A1 | 12/2003 | Kline et al. | |
| 2005/0092554 A1* | 5/2005 | McGillin | B65D 71/0088 186/52 |
| 2005/0209576 A1 | 9/2005 | Hirotsu | |
| 2006/0058770 A1 | 3/2006 | Bohlen et al. | |
| 2006/0069372 A1 | 3/2006 | Chakravarty et al. | |
| 2007/0062851 A1 | 3/2007 | Schulz et al. | |
| 2007/0083178 A1 | 4/2007 | Nash | |
| 2007/0233031 A1 | 10/2007 | Benson et al. | |
| 2008/0140039 A1 | 6/2008 | Snell | |
| 2008/0248239 A1 | 10/2008 | Pomeroy | |
| 2008/0312617 A1 | 12/2008 | Hundorf et al. | |
| 2008/0312619 A1 | 12/2008 | Ashton et al. | |
| 2008/0312624 A1 | 12/2008 | Hundorf | |
| 2009/0118689 A1 | 5/2009 | Lawson | |
| 2009/0299790 A1 | 12/2009 | Devarajan et al. | |
| 2011/0073513 A1 | 3/2011 | Weisman et al. | |
| 2011/0094979 A1* | 4/2011 | Lowery | B65D 71/0096 211/49.1 |
| 2011/0295575 A1 | 12/2011 | Levine et al. | |
| 2012/0226624 A1 | 9/2012 | Song et al. | |

FOREIGN PATENT DOCUMENTS

| | | |
|---|---|---|
| JP | 2003/335416 A | 11/2003 |
| WO | WO 94/00362 A1 | 1/1994 |
| WO | WO 95/16746 | 6/1995 |

OTHER PUBLICATIONS

All Office Actions, Responses and Claims for U.S. Appl. No. 12/890,800.
All Office Actions, Responses and Claims for U.S. Appl. No. 12/893,342.
All Office Actions, Responses and Claims for U.S. Appl. No. 14/063,446.
All Office Actions, Responses and Claims for U.S. Appl. No. 14/865,502.
All Office Actions, Responses and Claims for U.S. Appl. No. 16/141,238.
U.S. Appl. No. 14/063,446, filed Oct. 25, 2013, Paul Thomas Weisman.

* cited by examiner

METHOD OF MAXIMIZING SHIPPING EFFICIENCY OF ABSORBENT ARTICLES

FIELD OF THE INVENTION

The present disclosure relates generally to absorbent products, and more particularly, to methods of maximizing product delivery and shipping of absorbent articles having a substantially airfelt free absorbent core.

BACKGROUND OF THE INVENTION

Absorbent articles, such as disposable diapers, pant style diapers, training pants, adult incontinence undergarments, absorbent inserts, and the like absorb and contain body exudates.

Such absorbent articles are intended to prevent body exudates from soiling, wetting, or otherwise contaminating clothing or other articles, such as bedding, that come into contact with a wearer of the absorbent articles. Absorbent articles may be worn for several hours in a dry state or in a urine (or other body exudates) loaded state. Efforts are made to constantly improve the fit and comfort of such absorbent articles both in the wet and dry state.

Many current absorbent articles, particularly those with airfelt (or cellulose) absorbent cores are soft and flexible when first placed in an undergarment, but become more stiff when wet. Such flexible-then stiff characteristics are seen in absorbent articles with other types of cores as well. Additionally, such airfelt (or cellulose) absorbent articles are typically bulky. Overall, traditional absorbent articles that utilize airfelt (or cellulose) are bulky and somewhat uncomfortable to wear.

Moreover, such airfelt (or cellulose) absorbent articles are inefficient to ship as the large amount of airspace in such articles (for example, between the cellulose fibers) translates into fewer absorbent articles per package and fewer packages per box. While product compression may increase packing efficiency of airfelt (or cellulose) absorbent articles, over compression reduces the absorbency effectiveness of such absorbent articles. Additionally, over compression can reduce aesthetic appeal of such absorbent articles by making the product stiff and uncomfortable to wear, or by reducing the apparent softness of individual components of the absorbent article, such as the absorbent core. Quite often, when absorbent pads containing cellulose are compressed to achieve a thin form, hard spots develop within the pads, thereby resulting in a stiffer pad and a lack of uniformity in the absorbent material.

Due to the high volume/weight ratio of traditional airfelt absorbent articles, most often shipping and packing of such articles is limited by volume instead of weight. In other words, a maximum container or vehicle volume is reached before a maximum container or vehicle weight capacity is reached when packing and/or shipping the traditional airfelt absorbent articles. This results in a shipping inefficiency due to the fact that the maximum weight bearing capacity of the container or vehicle is not being fully utilized. Essentially, shipping capacity is lost due to the amount of air within the absorbent articles that are being shipped.

Improvements have been made to absorbent articles, such as disposable diapers, by including an absorbent polymer material (sometimes known as superabsorbent polymers), such as an absorbent particulate polymer material. Absorbent particulate polymer material absorbs liquid and swells and may be particularly effective when the absorbent particulate polymer is disposed in a particular pattern, arrangement, or matrix that optimizes absorbency, fit and/or comfort. Combinations of airfelt cores and absorbent polymer materials produce diapers that are thinner, more flexible, and more absorbent than previous diapers. This type of diaper construction is now prevalent and has been in use for some time. However, these diapers are still viewed to some extent as being bulky, stiff when wet, and inefficient to ship to various store locations.

It is therefore desirable to have an even thinner, less bulky diaper that is more comfortable to use, remains flexible when wet, and more cost effective to ship to various store locations. One option to reduce bulk is to reduce or eliminate airfelt from the absorbent core. The difficulty with this approach is that it would also necessitate the absorbent particulate polymer material remaining fixed in its intended location within the absorbent article without the airfelt core to help immobilize the material, regardless of whether the absorbent article is dry or wet. Several recent publications have disclosed diapers with reduced or eliminated airfelt cores combined with immobilized absorbent particulate polymer materials. For example, an absorbent article having a substantially airfelt free absorbent core is disclosed in U.S. Patent Publication No. 2008/0312617, which is hereby incorporated by reference herein.

In addition, typical computerized pallet loading software cannot improve loading of absorbent articles beyond a characteristic volume/weight ratio based on assumed inherent properties of the product being shipped. Such known computerized pallet loading software usually includes assumptions that continuous improvements in size and material reduction of absorbent articles will yield ever increasing shipping efficiency. However, such known computerized pallet loading software does not account for optimization processes that produce synergistic benefits associated with discontinuous improvements in product performance and physical parameters such as compressibility. As a result, known computerized pallet loading software fails to fully optimize shipping efficiency for most absorbent articles.

While the aforementioned application discloses an absorbent core for an absorbent article having a substantially airfelt free absorbent core, a need still exists for a mechanism to avoid hard, stiff spots in the article upon compressing to fit in a package. There further exists a need for a mechanism to fully optimize product delivery and shipping for such articles (optimization from the point of view of more articles per unit volume and less packaging per number of articles packed). These types of shipping efficiencies reduce the environmental impact of shipping such articles by reducing the number of pallets and the number of trucks needed to ship the articles to various store locations and warehouses.

SUMMARY OF THE INVENTION

In one embodiment, a shipping optimization process for absorbent articles having a substantially airfelt free absorbent core is disclosed. The shipping optimization process includes the steps of: identifying an optimized diaper; identifying an optimized bag for holding two or more optimized diapers; identifying an optimized box for holding two or more optimized bags; identifying an optimized pallet and arranging the optimized boxes thereon; and identifying an optimized load plan for a vehicle and arranging the optimized pallets therein. The vehicle has a calculated Load Factor of from about 0.75 to about 1.0 when the vehicle is loaded with the optimized pallets.

BRIEF DESCRIPTION OF THE DRAWINGS

While the specification concludes with claims which particularly point out and distinctly claim the subject matter that is regarded as the invention, it is believed the various embodiments will be better understood from the following description taken in conjunction with the accompanying drawings, in which:

Figure 1:
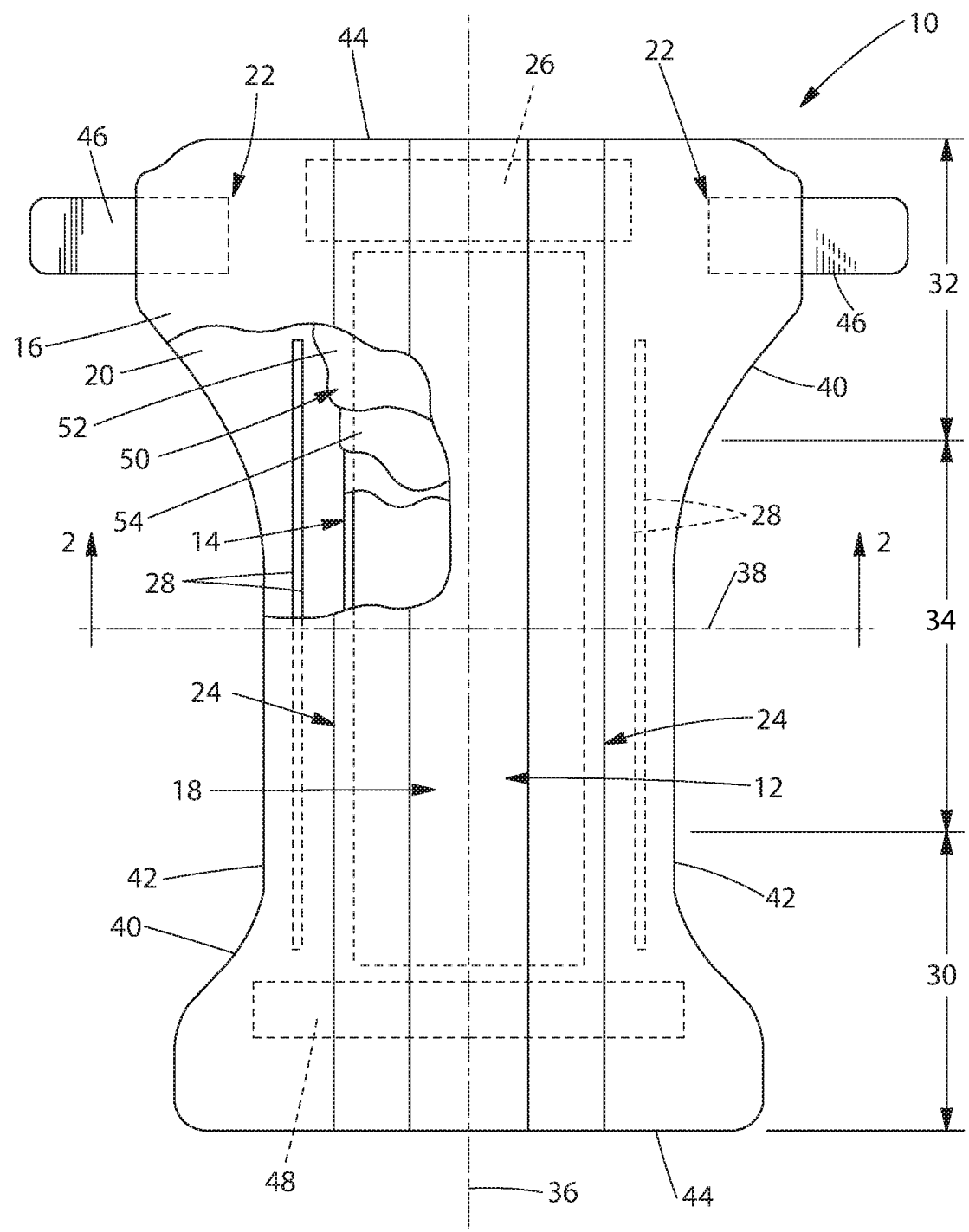
FIG. 1 is a plan view of an absorbent article having a substantially airfelt free absorbent core.

The figures herein are not necessarily drawn to scale.

DETAILED DESCRIPTION OF THE INVENTION

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, and adult incontinence undergarments.

"Absorbent core" means a structure typically disposed between a topsheet and backsheet of an absorbent article for absorbing and storing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core may be substantially cellulose free. The absorbent core includes the one or more substrates, the absorbent polymer material, the thermoplastic composition, optionally the cover layer and optionally auxiliary glue.

"Absorbent polymer material," "absorbent gelling material," "AGM," "superabsorbent," and "superabsorbent material" are used herein interchangeably and refer to substantially water-insoluble polymer particles that can absorb at least 5 times their weight of an aqueous 0.9% saline solution by way of an osmotic mechanism.

"Absorbent particulate polymer material" is used herein to refer to an absorbent polymer material which is in particulate form so as to be flowable in the dry state.

"Absorbent particulate polymer material area" as used herein refers to the area of the core wherein the first substrate and second substrate are separated by a multiplicity of superabsorbent particles. A boundary of the absorbent particulate polymer material area is defined by perimeters of overlapping shapes. There may be some extraneous superabsorbent particles outside of the perimeter between the first substrate and second substrate.

"Acquisition system" means a structure serving as a temporary reservoir for body fluids until the absorbent core can absorb the fluids. The acquisition system may be in direct contact with the absorbent core and resides between topsheet and the backsheet. The acquisition system may comprise a single layer or multiple layers, such as an upper acquisition layer facing towards the wearer's skin and a lower acquisition layer facing the garment of the wearer. The acquisition system may function to receive a surge of liquid, such as a gush of urine.

"Airfelt" and "Cellulose" are used interchangeably herein and refer to comminuted wood pulp, which is a form of cellulosic fiber.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Infant" diaper refers to an absorbent article generally intended for babies that are from about 0 to 6 months old. Within this group of diapers, 4 sizes are common; premature infants (up to about 6 lbs), newborn infants (up to about 10 lbs), size 1 infants (generally from about 8 to 14 lbs), and size 2 infants (generally from about 12 to 18 lbs). It is common for design features of this type of diaper to focus on benefits such as softness and/or gentleness to skin.

"Baby" diaper refers to an absorbent article generally intended for babies that are from about 6 to 12 months old. Within this group of diapers, 5 sizes are common; size 3 (from about 16 to 28 lbs), size 4 (from about 22 to 37 lbs), size 5 (greater than about 27 lbs), size 6 (greater than about 35 lbs), and size 7 (greater than about 41 lbs). It is common for design features of this type of diaper to focus on benefits such as fit and stretch, thereby allowing the baby more flexibility in crawling or walking.

"Toddler" diaper refers to an absorbent article generally intended for babies that are older than about 12 months, and may be in life stage where they are learning to use a toilet facility. Within this group, there are 3 common sizes; size 4 (from about 16 to 34 lbs), size 5 (from about 30 to 40 lbs), and size 6 (greater than about 37 lbs). It is common for design features of this type of diaper to focus on benefits such as fit and ease of placement/removal, thereby allowing the baby more convenience as they are trained on toilet facility usage. These diapers may be designed as pants or training pants, as defined below, or may simply be larger size diapers. The overlapping weight ranges for the various sizes described above are to accommodate the various size and shapes of babies within each stage of development.

"Pant" or "training pant," as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants." Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999, each of which is hereby incorporated by reference.

"Substantially cellulose free" or "substantially airfelt free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core. For example, the % by weight cellulose fiber for an absorbent core is calculated based upon using the total weight of absorbent particulate polymer material and cellulose fiber found in the absorbent core.

"Substantially continuously distributed" as used herein indicates that within the absorbent particulate polymer material area, the first substrate and second substrate are separated by a multiplicity of superabsorbent particles. It is recognized that there may be minor incidental contact areas between the first substrate and second substrate within the absorbent particulate polymer material area. Incidental contact areas between the first substrate and second substrate may be intentional or unintentional (e.g. manufacturing artifacts) but do not form geometries such as pillows, pockets, tubes, quilted patterns and the like.

"Thermoplastic adhesive material" as used herein is understood to comprise a polymer composition from which fibers are formed and applied to the superabsorbent material with the intent to immobilize the superabsorbent material in both the dry and wet state. The thermoplastic adhesive material of the present invention forms a fibrous network over the superabsorbent material.

"Thickness" and "caliper" are used herein interchangeably.

"In-Bag Compression" as used herein is one minus the height of a stack of 10 diaper pads in millimeters, measured while under compression within a poly-bag (In-Bag Stack Height), divided by the height of a stack of 10 diaper pads of the same type before compression, multiplied by 100; i.e., (1−In-Bag Stack Height/stack height before compression)× 100, reported as a percentage.

"Weight efficiency" as used herein refers to the net product and package weight of a transportation vehicle, such as a semi-trailer and tractor combination, divided by the maximum legal weight capacity of the vehicle on a percent basis. This weight efficiency is a numerical representation of the loading efficiency of a transportation vehicle in fully utilizing its maximum legally allowed weight capacity.

"Volume efficiency" as used herein refers to the net product and package volume of a transportation vehicle, such as a semi-trailer and tractor combination, divided by the volume capacity of the vehicle on a percent basis. This volume efficiency is a numerical representation of the loading efficiency of a transportation vehicle in fully utilizing its maximum physical space intended for transporting products.

"Load factor" as used herein refers to the ratio of weight efficiency divided by volume efficiency for a transportation vehicle, such as a semi-trail and tractor combination, and is a numerical representation of how well a load of absorbent articles is optimized for both the weight and volume capacities of a particular transportation vehicle.

An absorbent article having a substantially airfelt free absorbent core is disclosed in U.S. Patent Publication No.

2008/0312617, owned by The Procter and Gamble Company, and hereby incorporated by reference herein. An absorbent article having a substantially airfelt free absorbent core, such as a diaper, is shown in FIG. 1. The diaper 10 is shown in its flat out, uncontracted state (i.e., without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. A periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 10 may also include such other features as are known in the art including front and rear ear panels, waist cap features, elastics and the like to provide better fit, containment and aesthetic characteristics. Such additional features are well known in the art and are e.g., described in U.S. Pat. Nos. 3,860,003 and 5,151,092, both of which are hereby incorporated by reference.

In order to keep the diaper 10 in place about the wearer, at least a portion of the first waist region 30 may be attached by the fastening members 46 to at least a portion of the second waist region 32 to form leg opening(s) and an article waist. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements. In one embodiment, fastening member 46 may include tape tab fasteners, hook and loop fasteners, mushroom and loop fasteners, snaps, pins, belts and the like, and combinations thereof. Typically, fastening member 46 is configured to be refastenable or re-closable. In some embodiments, fastening member 46 may be adapted to engage or otherwise join with a fastening element, for example, the outer covering 16. In other embodiments, the fastening element may be a fastener landing zone 48. Fastener landing zone 48 may be a piece of loop material located on the outer covering 16 in the front waist region 30 and is adapted to engage a hook-type fastening member 46. In alternative embodiments, the landing zone 48 may be a film adapted to engage with a tape tab fastening member 46.

The diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. The materials making up the fastening device may be flexible. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the topsheet 18, the backsheet 20, and the absorbent core 14 may be assembled in a variety of well-known configurations, some diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999, each of which is hereby incorporated by reference.

The topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993, each of which is hereby incorporated by reference.

The backsheet 26 may be joined with the topsheet 18. The backsheet 20 may prevent the exudates absorbed by the absorbent core 14 and contained within the diaper 10 from soiling other external articles that may contact the diaper 10, such as bed sheets and undergarments. The backsheet 26 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E.I. DuPont, which is hereby incorporated by reference. Other breathable backsheets including nonwoven webs and apertured formed films are described in U.S. Pat. No. 5,571,096 issued to Dobrin et al. on Nov. 5, 1996, which is hereby incorporated by reference.

The backsheet may have a water vapor transmission rate (WVTR) of greater than about 2000 g/24 h/m$^2$, greater than about 3000 g/24 h/m$^2$, greater than about 5000 g/24 h/m$^2$, greater than about 6000 g/24 h/m$^2$, greater than about 7000 g/24 h/m$^2$, greater than about 8000 g/24 h/m$^2$, greater than about 9000 g/24 h/m$^2$, greater than about 10000 g/24 h/m$^2$, greater than about 11000 g/24 h/m$^2$, greater than about 12000 g/24 h/m$^2$, greater than about 15000 g/24 h/m$^2$, measured according to WSP 70.5 (08) at 37.8.° C. and 60% Relative Humidity.

Figure 2:
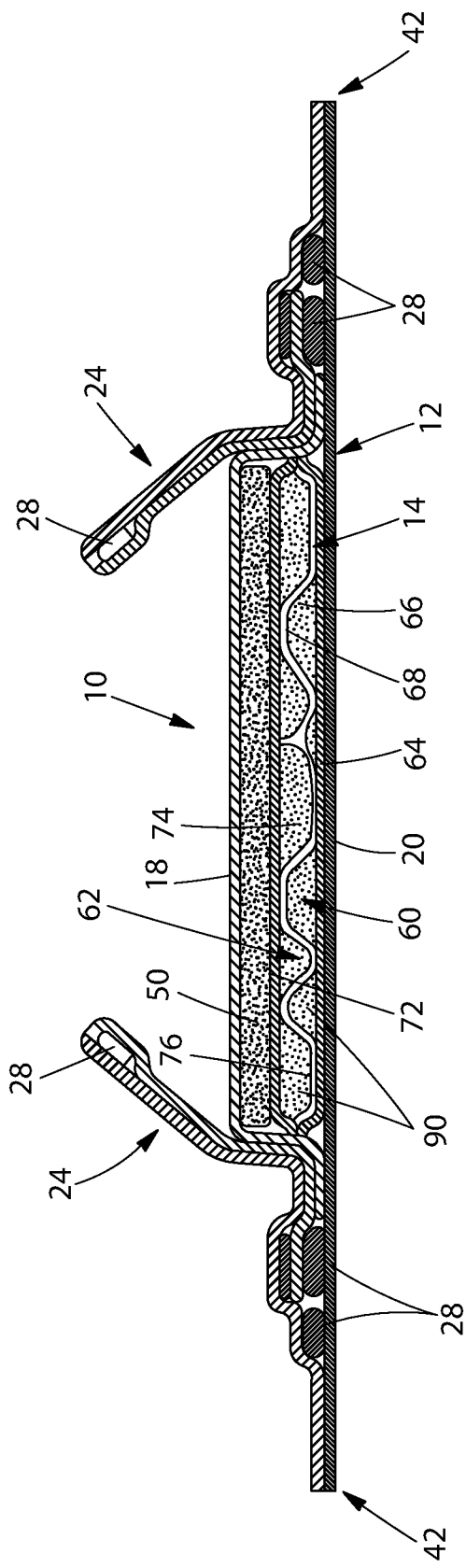
FIG. 2 is a cross sectional view of the absorbent article of FIG. 1.

FIG. 2 shows a cross section of the diaper 10 of FIG. 1 taken along the sectional line 2-2 of FIG. 1. Starting from the wearer facing side, the diaper 10 may comprise the topsheet 18, the components of the absorbent core 14, and the backsheet 20. The diaper 10 may also comprise an acquisition system 50 disposed between the liquid permeable topsheet 18 and the backsheet 20. In one embodiment, the diaper 10 may comprise an acquisition system 50 disposed between the liquid permeable topsheet 18 and a wearer facing side of the absorbent core 14. The acquisition system 50 may be in direct contact with the absorbent core 14. The acquisition system 50 may comprise a single layer or multiple layers (not shown), such as an upper acquisition layer 52 facing towards the wearer's skin and a lower acquisition layer 54 facing the garment of the wearer. The acquisition system 50 may function to receive a surge of liquid, such as a gush of urine. In other words, the acquisition system 50 may serve as a temporary reservoir for liquid until the absorbent core 14 can absorb the liquid.

The lower acquisition layer 54 may have a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. The lower acquisition layer 54 may have a maximum uptake of about 10 g/g.

A relevant attribute of the upper acquisition layer 54 is its Median Desorption Pressure, MDP. The MDP is a measure of the capillary pressure that is required to dewater the lower acquisition layer 54 to about 50% of its capacity at 0 cm capillary suction height under an applied mechanical pressure of 0.3 psi. Generally, a relatively lower MDP may be useful. The lower MDP may allow the lower acquisition layer 54 to more efficiently drain the upper acquisition material. The ability of the lower acquisition layer 54 to move liquid vertically via capillary forces will be directly impacted by gravity and the opposing capillary forces associated with desorption of the upper acquisition layer. Minimizing these capillary forces may positively impact the performance of the lower acquisition layer 54. However, the lower acquisition layer 54 may also have adequate capillary absorption suction in order to drain the layers above (upper acquisition layer 52 and topsheet 18, in particular) and to temporarily hold liquid until the liquid can be partitioned away by the absorbent core components. Therefore, the lower acquisition layer 54 may have a minimum MDP of greater than 5 cm. Further, the lower acquisition layer 54 has an MDP value of less than about 20.5 cm H$_2$O, or less than about 19 cm H$_2$O, or less than about 18 cm H$_2$O to provide for fast acquisition.

Figure 3:
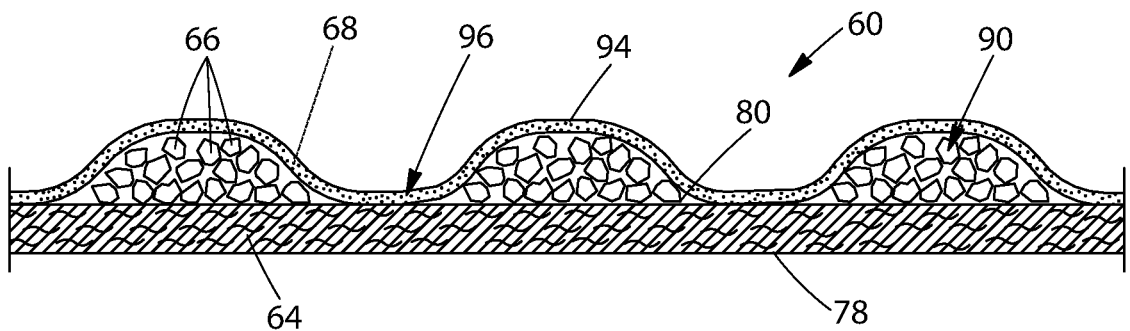
FIG. 3 is a partial cross sectional view of an absorbent core layer of the absorbent article of FIGS. 1 and 2.
Figure 4:
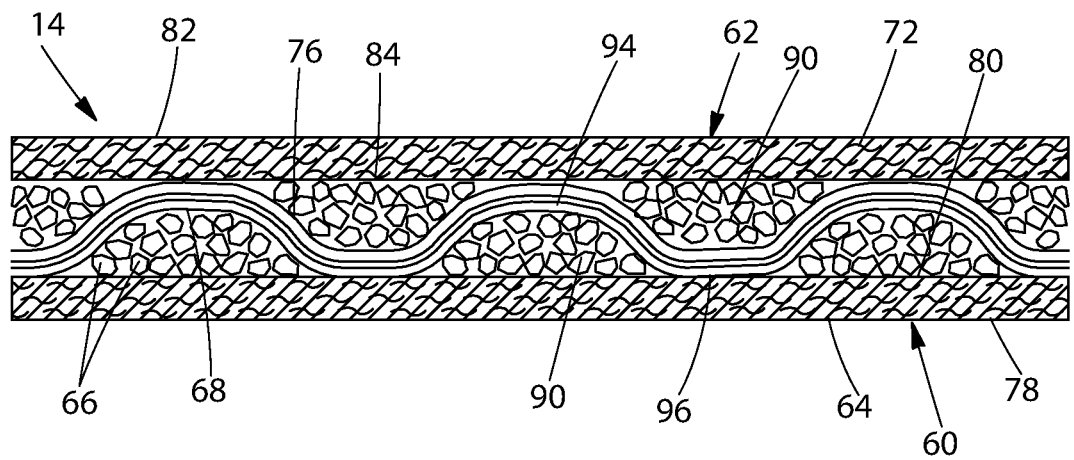
FIG. 4 is a partial cross sectional view of an absorbent core in accordance with another embodiment.

In one embodiment, the absorbent core 14 as shown in FIGS. 1, 2 and 4 generally is disposed between the topsheet 18 and the backsheet 20 and comprises two layers, a first absorbent layer 60 and a second absorbent layer 62. As best shown in FIG. 3, the first absorbent layer 60 of the absorbent core 14 comprises a substrate 64, an absorbent particulate polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. The first absorbent layer 60 of the absorbent core 14 may also include a cover layer (not shown) on the thermoplastic composition 68.

Likewise, as best illustrated in FIGS. 2 and 4, the second absorbent layer 62 of the absorbent core 14 may also include a substrate 72, an absorbent particulate polymer material 74 on the second substrate 72, and a thermoplastic composition 76 on the absorbent particulate polymer material 74 and at least a portion of the second substrate 72 for immobilizing the absorbent particulate polymer material 74 on the second substrate 72. Although not illustrated, the second absorbent layer 62 may also include a cover layer.

The substrate 64 of the first absorbent layer 60 may be referred to as a dusting layer and has a first surface 78 (FIG. 3) which faces the backsheet 20 of the diaper 10 and a second surface 80 which faces the absorbent particulate polymer material 66. Likewise, the substrate 72 of the second absorbent layer 62 may be referred to as a core cover and has a first surface facing the topsheet 18 of the diaper 10 and a second surface facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

The substrates 64 and 72 of the first and second absorbent layers 60 and 62 may be a non-woven material. The nonwovens may be porous and may have a pore size of about 32 microns.

As illustrated in FIGS. 2 and 4, the absorbent particulate polymer material 66 and 74 is deposited on the respective substrates 64 and 72 of the first and second absorbent layers 60 and 62 in clusters 90 of particles to form a grid pattern comprising land areas 94 and junction areas 96 between the land areas 94. As defined herein, land areas 94 are areas where the thermoplastic adhesive material does not contact the nonwoven substrate or the auxiliary adhesive directly; junction areas 96 are areas where the thermoplastic adhesive material does contact the non-woven substrate or the auxiliary adhesive directly. The junction areas 96 in the grid pattern contain little or no absorbent particulate polymer material 66 and 74. The land areas 94 and junction areas 96 can have a variety of shapes including, but not limited to, circular, oval, square, rectangular, triangular, any polygon shape, and the like.

The size of the land areas 94 may vary. The width of the land areas 94 may range from about 8 mm to about 12 mm. The junction areas 96, on the other hand, may have a width or larger span of less than about 5 mm, less than about 3 mm, less than about 2 mm, less than about 1.5 mm, less than about 1 mm, or less than about 0.5 mm.

The junction areas 96 can be disposed in a regular or irregular pattern. In one embodiment, the arrangement of land areas 94 and junction areas 96 forms an angle which may be 0 degrees, greater than 0 degrees, or 15 to 30 degrees, or from about 5 to about 85 degrees, or from about 10 to about 60 degrees, or from about 15 to about 30 degrees.

The first and second absorbent layers 60 and 62 may be combined together to form the absorbent core 14 such that the layers may be offset such that the absorbent polymer material 66 and 74 is substantially continuously distributed across the absorbent polymer area. In a certain embodiment, absorbent polymer material 66 and 74 is substantially continuously distributed across the absorbent polymer material area despite absorbent polymer material 66 and 74 discontinuously distributed across the first and second substrates 64 and 72 in clusters 90. In a certain embodiment, the absorbent layers may be offset such that the land areas 94 of the first absorbent layer 60 face the junction areas 96 of the second absorbent layer 62 and the land areas of the second absorbent layer 62 face the junction areas 96 of the first absorbent layer 60. When the land areas 94 and junction areas 96 are appropriately sized and arranged, the resulting combination of absorbent polymer material 66 and 74 is a substantially continuous layer of absorbent polymer material across the absorbent polymer material area of the absorbent core 14 (i.e. first and second substrates 64 and 72 do not form a plurality of pockets, each containing a cluster 90 of absorbent particulate polymer material 66 therebetween).

In a certain embodiment, the amount of absorbent polymer material 66 and 74 may vary along the length of the core. The amount of absorbent polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In a particular embodiment, the absorbent core 14 comprises first and second substrates 64 and 72, the absorbent polymer material 66 and 74, and the thermoplastic composition 68 and 76. In such an embodiment, the absorbent core 14 is substantially cellulose free.

It has been found that, for most absorbent articles such as diapers, the liquid discharge occurs predominately in the front half of the diaper. The front half of the absorbent core 14 should therefore comprise most of the absorbent capacity of the core. Thus, according to certain embodiments, the front half of said absorbent core 14 may comprise more than about 60% of the superabsorbent material, or more than about 65%, 70%, 75%, 80%, 85%, or 90% of the superabsorbent material. The front half is defined as the region between the midpoint on the longitudinal axis 36 and the end edge 44 disposed in the first waist region 30.

In certain embodiments, the absorbent core 14 may further comprise any absorbent material that is generally compressible, conformable, non-irritating to the wearer's skin, and capable of absorbing and retaining liquids such as urine and other certain body exudates. In such embodiments, the absorbent core 14 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 14 may further comprise minor amounts (typically less than about 10%) of materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

In one embodiment, the thermoplastic adhesive material 68 and 76 may serve to cover and at least partially immobilize the absorbent polymer material 66 and 74. In one embodiment, the thermoplastic adhesive material 68 and 76 can be disposed essentially uniformly within the absorbent polymer material 66 and 74, between the polymers. However, in a certain embodiment, the thermoplastic adhesive material 68 and 76 may be provided as a fibrous layer which is at least partially in contact with the absorbent polymer material 66 and 74 and partially in contact with the substrate layers 64 and 72 of the first and second absorbent layers 60 and 62. FIG. 4 shows such a structure, and in that structure, the absorbent polymer material 66 and 74 is provided as a discontinuous layer, and a layer of fibrous thermoplastic adhesive material 68 and 76 is laid down onto the layer of absorbent polymer material 66 and 74, such that the thermoplastic adhesive material 68 and 76 is in direct contact with the absorbent polymer material 66 and 74, but also in direct contact with the second surfaces 80 and 84 of the substrates 64 and 72, where the substrates are not covered by the absorbent polymer material 66 and 74. This imparts an essentially three-dimensional structure to the fibrous layer of thermoplastic adhesive material 68 and 76, which in itself is essentially a two-dimensional structure of relatively small thickness, as compared to the dimension in length and width directions. In other words, the thermoplastic adhesive material 68 and 76 undulates between the absorbent polymer material 66 and 74 and the second surfaces of the substrates 64 and 72.

Thereby, the thermoplastic adhesive material 68 and 76 may provide cavities to cover the absorbent polymer material 66 and 74, and thereby immobilizes this material. In a further aspect, the thermoplastic adhesive material 68 and 76 bonds to the substrates 64 and 72 and thus affixes the absorbent polymer material 66 and 74 to the substrates 64 and 72. Some thermoplastic adhesive materials will also penetrate into both the absorbent polymer material 66 and 74 and the substrates 64 and 72, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive materials may also provide a very good immobilization of absorbent material when the absorbent core 14 is dry. The thermoplastic adhesive material 68 and 76 may also be referred to as a hot melt adhesive.

Without wishing to be bound by theory, it has been found that those thermoplastic adhesive materials which are most useful for immobilizing the absorbent polymer material 66 and 74 combine good cohesion and good adhesion behavior.

Good adhesion may promote good contact between the thermoplastic adhesive material 68 and 76 and the absorbent particulate polymer material 66 and 74 and the substrates 64 and 72. Good cohesion reduces the likelihood that the adhesive breaks, in particular in response to external forces, and namely in response to strain. When the absorbent core 14 absorbs liquid, the absorbent polymer material 66 and 74 swells and subjects the thermoplastic adhesive material 68 and 76 to external forces. In certain embodiments, the thermoplastic adhesive material 68 and 76 may allow for such swelling, without breaking and without imparting too many compressive forces, which would restrain the absorbent polymer material 66 and 74 from swelling.

In accordance with certain embodiments, the thermoplastic adhesive material 68 and 76 may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or −6° C.>Tg<16° C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

In exemplary embodiments, the tackifying resin typically has a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%.

In certain embodiments, the thermoplastic adhesive material 68 and 76 is present in the form of fibers. In some embodiments, the fibers will have an average thickness of from about 1 to about 50 micrometers or from about 1 to about 35 micrometers and an average length of from about 5 mm to about 50 mm or from about 5 mm to about 30 mm. To improve the adhesion of the thermoplastic adhesive material 68 and 76 to the substrates 64 and 72 or to any other layer, in particular any other non-woven layer, such layers may be pre-treated with an auxiliary adhesive.

The absorbent core 14 may also comprise an auxiliary adhesive which is not illustrated in the figures. The auxiliary adhesive may be deposited on the first and second substrates 64 and 72 of the respective first and second absorbent layers 60 and 62 before application of the absorbent particulate polymer material 66 and 74 for enhancing adhesion of the absorbent particulate polymer materials 66 and 74 and the thermoplastic adhesive material 68 and 76 to the respective substrates 64 and 72. The auxiliary glue may also aid in immobilizing the absorbent particulate polymer material 66 and 74 and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary glue may be applied to the substrates 64 and 72 by any suitable means, but according to certain embodiments, may be applied in about 0.5 to about 1 mm wide slots spaced about 0.5 to about 2 mm apart.

In addition to being thin, flexible, absorbent, and more comfortable to wear, these types of absorbent articles have an unexpected benefit. These absorbent articles can be compressed to higher levels during production, packing, and storage than previous airfelt core absorbent articles without causing an in-use increase in product stiffness due to over compression. The increase in compressibility provides multiple cost-savings benefits; lower shipping costs lower storage/warehousing costs, reduced packaging costs, reduced shelving/stocking costs, lower disposal costs, etc. The increase in compressibility also provides smaller package sizes by reducing the in-bag stack thickness or in-bag stack height for unopened packages of absorbent articles resulting in more environmentally friendly packaging.

In one embodiment, absorbent products according to the present disclosure may have an in-bag stack height of less than or equal to about 80 mm according to the In-Bag Stack Height Test described herein. In another embodiment, absorbent products according to the present disclosure may have an in-bag stack height of less than about 78 mm and in another embodiment of less than 76 mm according to the In-Bag Stack Height Test described herein. In another embodiment, absorbent products may have an In-Bag Stack Height of from about 72 mm to about 80 mm and in yet another embodiment of from about 74 mm to about 78 mm.

Figure 5A:
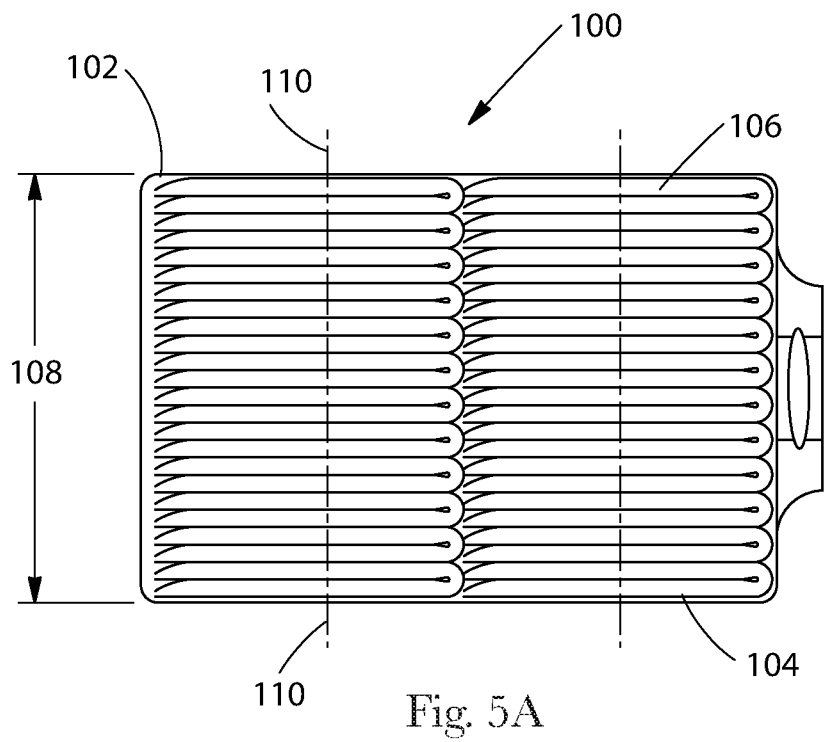
FIG. 5a is side view of a package of absorbent articles in accordance with one embodiment showing the package width. The outer surface is illustrated as transparent for purposes of clarity.

Typically, products such as absorbent articles are not sold individually, but rather are sold in packages containing a plurality of absorbent articles. For example, smaller absorbent articles, such as infant diapers may be sold in packages of thirty or more diapers, while toddler training pants may be sold in packages of twelve to eighteen training pants. In one embodiment, the absorbent articles are packaged in a poly bag. In another embodiment, the package may be a plastic "shrink-wrap" container. As shown in FIG. 5a, package 100 is a poly bag. Package 100 has an interior space 102, an exterior surface 112 and a height, width, and depth dimension. Package 100 may be any shape known in the art. For example, the package may have a polyhedral shape defining or forming a polyhedral enclosure. Interior 102 defines an interior space for containing absorbent articles 104. In one embodiment, the absorbent articles may all be identical to one another.

The absorbent articles 104 are arranged to form a stack 106 within interior 102. The articles may be stacked in any direction. As used herein, the term "stack" means an orderly pile. For example, the articles may be stacked vertically, horizontally, or at any angle inside the interior of the package. As shown in FIG. 5a, package 100 has a package width 108 that is defined as the maximum distance between the two highest bulging points along the same compression stack axis 110 of the package. Absorbent articles according to the present disclosure can be bi-folded, as shown in FIG.

Figure 7A:
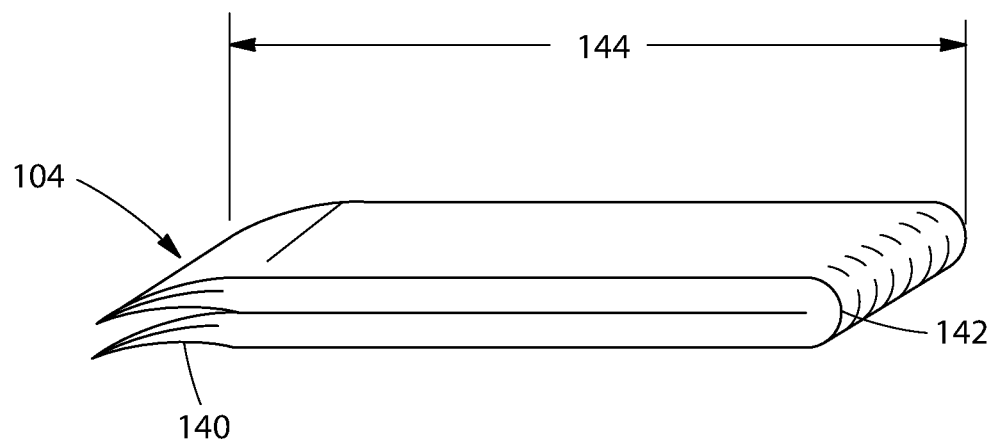
FIG. 7a is a side view of an absorbent article that has been bi-folded.
Figure 7B:
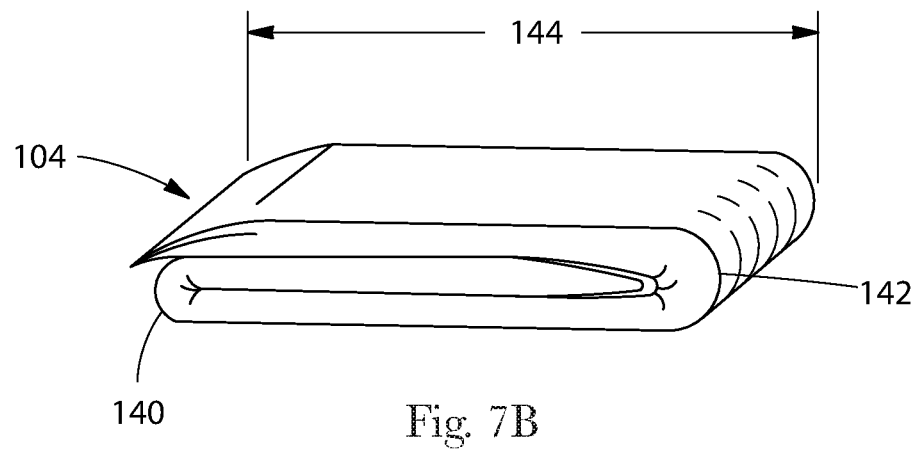
FIG. 7b is a side view of an absorbent article that has been tri-folded.
Figure 8:
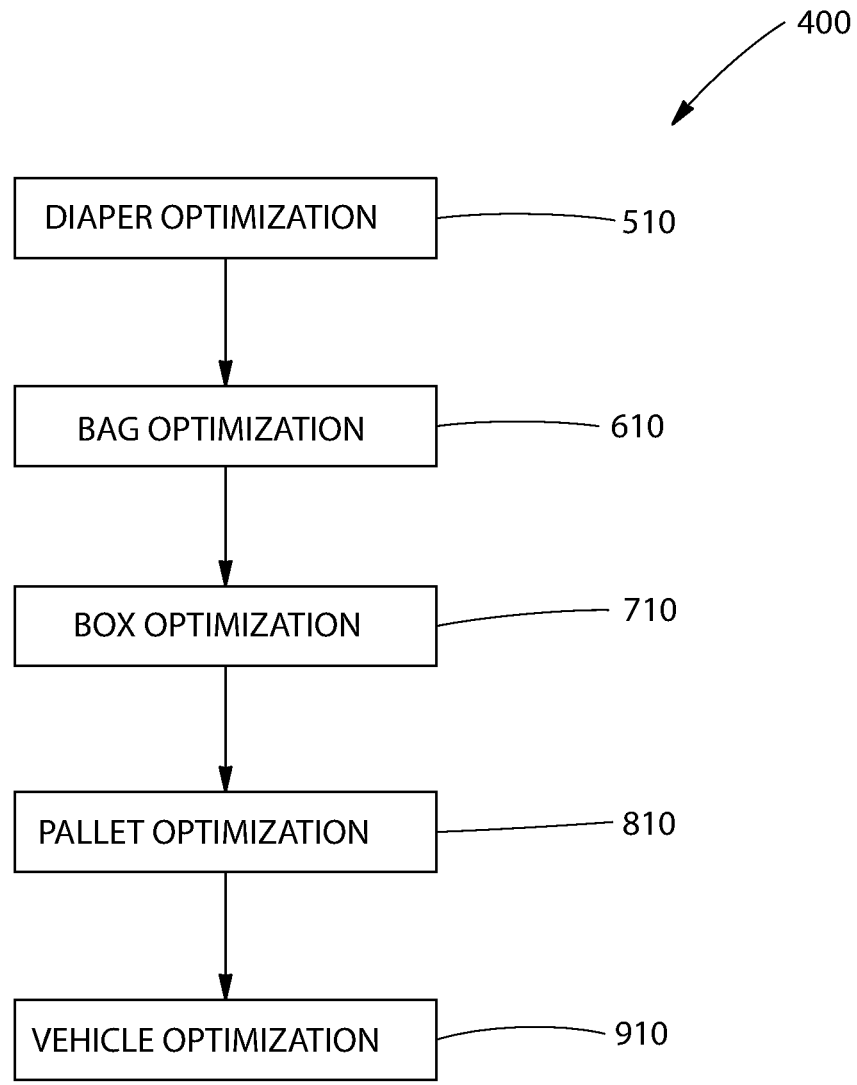
FIG. 8 is a logic diagram of a shipping optimization process in accordance with the teachings of the disclosure.

7a, or tri-folded, as shown in FIG. 7b. Other suitable folding techniques are also contemplated, for example, rolled or double bi-folded. The package 100 may also include a mechanism or means for accessing the interior space, for example, a gusset, a line of perforations, tabs, adhesive openings or any other means known in the art.

Package 100 may be composed of different materials or may be composed of substantially the same type of material. Package 100 may be composed of one layer or a laminate. The material can comprise a blown or cast film in a blend of low density polyethylene and linear low density polyethylene, metallocenes, ethylene vinyl acetate, surlyn, polyethylene terephtalate, biaxially oriented polypropylene, and/or nylon.

The number of absorbent articles placed in a package depends on several factors, including for example, folded dimensions, weight and a target compressibility range. For instance, Infant diapers (0-6 months) are expected to have a very soft backsheet feel for consumers when they hold or cuddle with their baby. To prevent a reduction in backsheet softness, these diapers are normally only compressed to between 30-38% within the product package, also known as in-bag compression, based on the number of pads contained in the package.

Baby diapers (6-12 months) and Toddlers (12-24+ months) do not have the same backsheet softness requirements as mothers are not spending as much time holding and cuddling babies within this age group. Within this age group, the diaper performance requirements (beyond absorbency) primarily relate to stretch, flexibility, and fit, and are associated with babies learning to crawl and walk. Diaper stiffness is an important product attribute for these diapers, and can be negatively affected by over-compression of product within the package. These diapers are normally compressed to between about 50 and 57% within the product package. Compression of these diapers beyond 57% leads to overall diaper stiffness associated with core over-compression.

Pants and training pants (24+ months) are designed with a focus on change-ability. Ease of pulling on and off as well as side-opening features are the two most important elements of these diapers. Absorbency and softness are sacrificed in order to encourage potty training and to minimize product costs. Therefore, diapers in this range are occasionally over-compressed beyond 57% to reduce material and shipping costs. However, backsheet roughness and overall diaper stiffness are seen as product negatives with the pants category.

Surprisingly, we have found that with Baby and Toddler size substantially airfelt free diapers, the target compressibility range can be increased without adversely affecting key consumer aesthetic attributes of the diaper (stiffness/flexibility, softness, etc.). For example, absorbent products according to the present disclosure may have an in-bag compression of greater than or equal to about 58%. In another embodiment, absorbent products may have an in-bag compression of from about 58% to about 62%, in another embodiment of from about 58.5% to about 61.5% and in yet another embodiment of from about 59% to about 61%. Further, the in-bag compression for absorbent products having substantially airfelt free diapers can be increased, while at the same time reducing stiffness and increasing flexibility. In one embodiment, absorbent products according to the present disclosure may include absorbent articles having a longitudinal bending stiffness of less than or equal to about 355 N/m according to the Stiffness Test described herein. In another embodiment, absorbent products may include absorbent articles having a longitudinal bending stiffness of less than about 325 N/m and in another embodiment of less than about 310 N/m. In another embodiment, absorbent products may include absorbent articles having a longitudinal bending stiffness of from about 285 N/m to about 355 N/m and in another embodiment of from about 295 N/m to about 345 N/m.

The effects of over compression on diapers with airfelt cores, measured in terms of stiffness, is illustrated in Table 1 below:

TABLE 1

Longitudinal Bending Stiffness Results for Sample Diapers and Pants

| Example | Longitudinal Bending Stiffness (N/m) |
|---|---|
| 1 | 699 |
| 2 | 530 |
| 3 | 619 |
| 4 | 641 |
| 5 | 554 |
| 6 | 470 |
| 7 | 507 |
|  | Avg. 574 |
| 8 | 414 |
| 9 | 429 |
| 10 | 474 |
| 11 | 494 |
| 12 | Not recorded due to instrument malfunction |
| 13 | 392 |
| 14 | 437 |
|  | Avg. 440 |
| 15 | 528 |
| 16 | 579 |
| 17 | 582 |
| 18 | 427 |
| 19 | 539 |
| 20 | 446 |
| 21 | 553 |
|  | Avg. 522 |
| 22 | 286 |
| 23 | 325 |
| 24 | 325 |
| 25 | 355 |
| 26 | 299 |
| 27 | 285 |
| 28 | 286 |
|  | Avg. 309 |

Examples 1-7 are commercially available airfelt training pants sold by Kimberly-Clark Corporation under the trademark HUGGIES LEARNING DESIGN (size 3/4T; bag count 23; Lot # b1919719F 19.1).

Examples 8-14 are commercially available airfelt diapers sold by The Procter & Gamble Company under the trademark PAMPERS CRUISERS (size 5; bag count 28; Lot #9200U01766 05:16)

Examples 15-21 are commercially available airfelt diapers sold by The Procter & Gamble Company under the trademark PAMPERS CRUISERS (size 5; bag count 25; Lot #9242U01764 11:50). 10 of these diapers were removed from the bag and compressed under conditions similar to Examples 22-28, i.e. a height of 40 mm for 2 seconds (intended to simulate the compression during transfer from the manufacturing line to the bagger for absorbent articles in accordance with the present disclosure) and then held at a height of 74 mm for 24 hours (intended to simulate the compression while in-bag for absorbent articles in accordance with the present disclosure). This demonstrates that current airfelt diapers compressed under conditions similar to Examples 22-28, adversely affects product stiffness.

Examples 22-28 are embodiments of absorbent articles in accordance with the present disclosure (size 5; bag count 40; Lot #9244U01762X1504). These examples were less stiff and thus more flexible than the other comparative diapers and pants having airfelt cores from Examples 1-21 above.

Figure 6A:
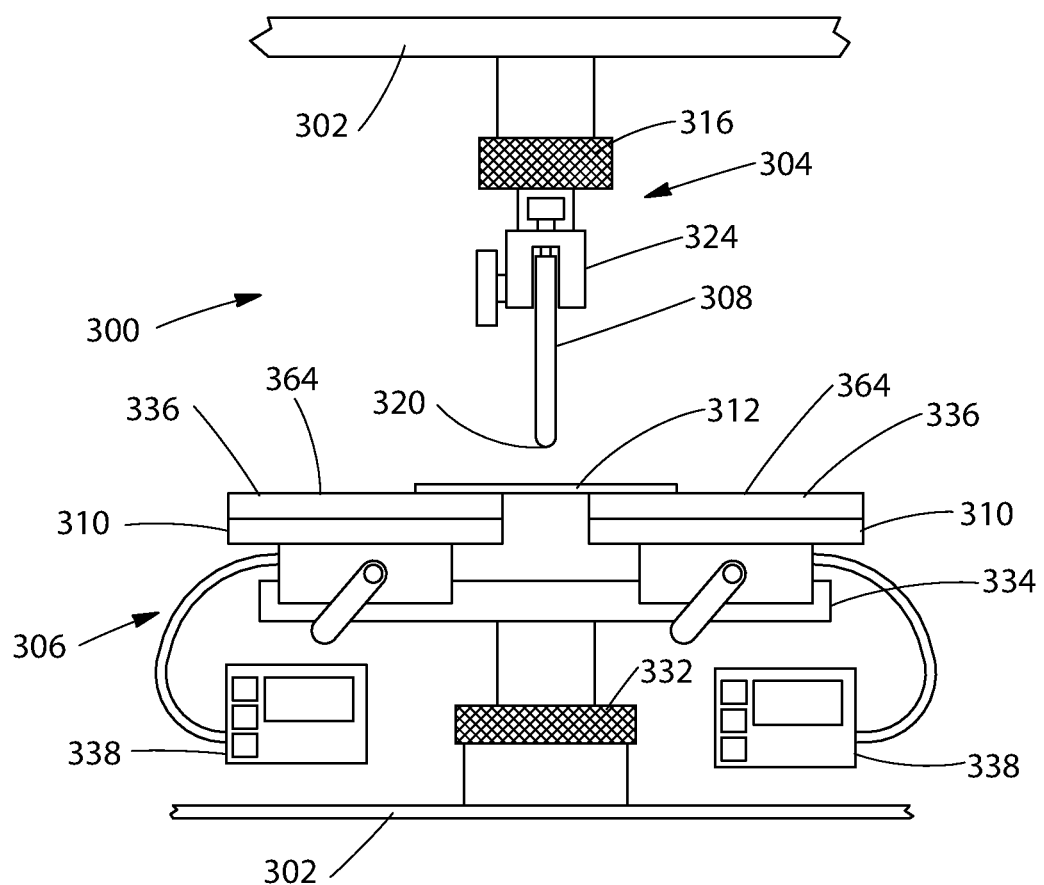
FIG. 6a is a front plan view showing a stiffness test apparatus with an upper fixture assembly and a lower fixture assembly.
Figure 6B:
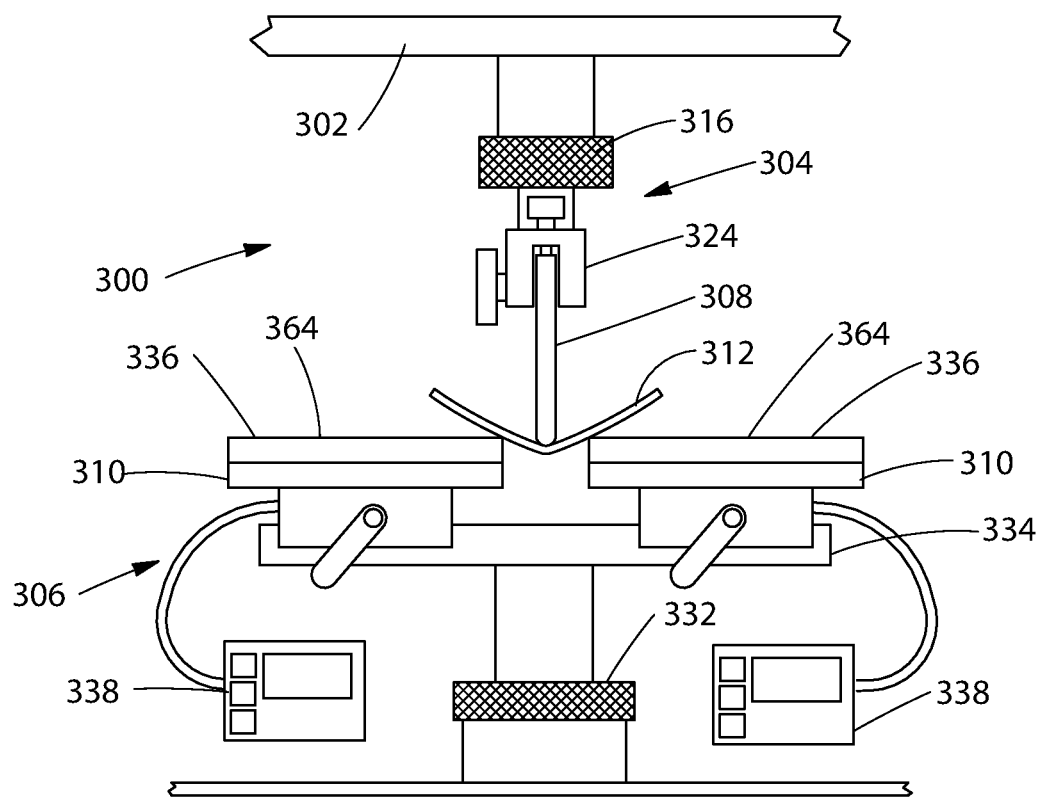
FIG. 6b is a front plan view showing the stiffness test apparatus with the upper fixture assembly engaging a test specimen.

Stiffness is measured by the following test. FIGS. 6a and 6b illustrate a Stiffness Test apparatus 300 used to measure the stiffness. The Stiffness Test apparatus 300 includes a constant rate of extension tensile tester 302 with computer interface (a suitable instrument is a MTS Alliance under Test Works 4 software, as available from MTS Systems Corp., Eden Prairie, Minn.) fitted with a 25 N load cell. The test apparatus 300 also includes an upper movable test fixture 304 and a lower stationary test fixture 306. A plunger blade 308 is used for the upper movable test fixture 304 and base support platforms 310 are used as the lower stationary test fixture 306. All testing is performed in a conditioned room maintained at 23° C.±2° C. and 50%±2% relative humidity. As discussed in more detail below, during stiffness testing, the upper fixture assembly 304 moves from a first position, such as shown in FIG. 7a, to a second position, such as shown in FIG. 7b, to engage and bend a test specimen 312 disposed on the lower stationary test fixture 306.

Components of the plunger blade 308 are made of aluminum to maximize the available load cell capacity. A shaft 314 is machined to fit the tensile tester and has a locking collar 316 to stabilize the plunger blade 308 and maintain alignment orthogonal to base support platforms 310. The plunger blade defines a length 318L of 300 mm long, a height 318H of 65 mm, and thickness 318T of 3.25 mm, and has a material contact edge 320 with a continuous radius 322 of 1.625 mm. A bracket 324 fitted with set screws 326 are used to level the blade and a main set screw 328 to firmly hold the plunger blade 308 in place after adjustment.

As shown in FIGS. 6a and 6b, the lower test fixture 306 is attached to the tensile tester 302 with a shaft 330 and locking collar 332. The two support platforms 310 are movably mounted on a rail 334. The two support platforms each have a test surface 336 having a width 336W of 85 mm and length of 300 mm (perpendicular to the plane of the drawing). The test surfaces 336 are made of polished stainless steel so as to have a minimal coefficient of friction. Each platform 310 has a digital position monitor 338 which reads the individual platform positions (to the nearest 0.01 mm), and set screws 340 to lock the positions of the platforms 310 after adjustment. The two platforms form a gap 342 with an adjustable gap width 344. The two platforms 310 are square at the gap edge and the plate edges must be parallel front to back. The surfaces 364 must be at the same height so as to be disposed within the same plane.

A test specimen 312 may include an absorbent article, shown for example, in FIG. 1. The following provides a description of the steps that are followed to carry out a Stiffness Test to determine the longitudinal bending stiffness of a test specimen 312. To test the longitudinal bending stiffness of a test specimen, the plunger blade is accurately aligned (±0.02 mm) so that the plunger blade is orthogonal to top surfaces 364 of the support platforms 310 and exhibits no skew relative to gap edges 366. Using the position monitors 338, the width 344 of the gap 342 is accurately set to 50.00±0.02 mm between the two gap edges 366 of the support platforms 310, with the plunger blade 308 accurately (±0.02 mm) centered in the gap 342. The tensile tester is programmed for a compression test. The gage length is set from the material contact edge 320 of the plunger blade 308 to the top surfaces 364 of the support platforms 310 to 25 mm. The crosshead is set to lower at 500 mm/min for a distance of 50 mm. The data acquisition rate is set to 200 Hz.

Test specimens are preconditioned at 23° C.±2° C. and 50%±2% relative humidity for 2 hours prior to testing. During preconditioning the specimens should remain compressed and sealed within its package until just before testing. The specimen is tested in the same folded configuration it was in the package and should not be tested more than once.

To test the longitudinal bending stiffness, specimen is placed flat onto the top surfaces 364 of the support platforms 310 over the gap 342 with the top side 358 facing upward. The test specimen is placed with the longitudinal axis 36 parallel to the length dimension of the plunger blade 308, and centered in the lateral 38 and the longitudinal 346 directions under the shaft 314 of the plunger blade. The load cell is zeroed and the tensile tester and the data acquisition are started.

The software is programmed to calculate the maximum peak force (N) and stiffness (N/m) from the force (N) versus displacement (m) curves. Stiffness is calculated as the slope of the force/displacement curve for the linear region of the curve, using a minimum line segment of at least 25% of the total peak force to calculate the slope. The stiffness is reported to the nearest 0.1 N/m. At least five samples are measured in this manner for a given product and the stiffness values are aggregated to calculate an average and standard deviation.

Consumers generally prefer smaller, more environmentally friendly packaging for products. As mentioned above, the increase in compressibility provides smaller package sizes and thus reduces the amount of packaging materials, for example, film material that is required per package of absorbent articles. One way to compare the amount of packaging materials used for absorbent articles is to calculate a bag or film utilization factor by measuring the package width, height and depth and calculating a surface area of the package utilizing the equation: Surface Area=(width×height×2)+(width×depth×2)+(height×depth×2). This package surface area is then divided by the bag pad count, i.e. the number of absorbent articles in the package, to give an area per pad result. However, such a calculation fails to account for differences associated with the size of diapers. Thus, one way to compare the bag utilization factor for different packages is to normalize for differences in Folded Stack Length of the absorbent articles within the package.

Figure 5B:
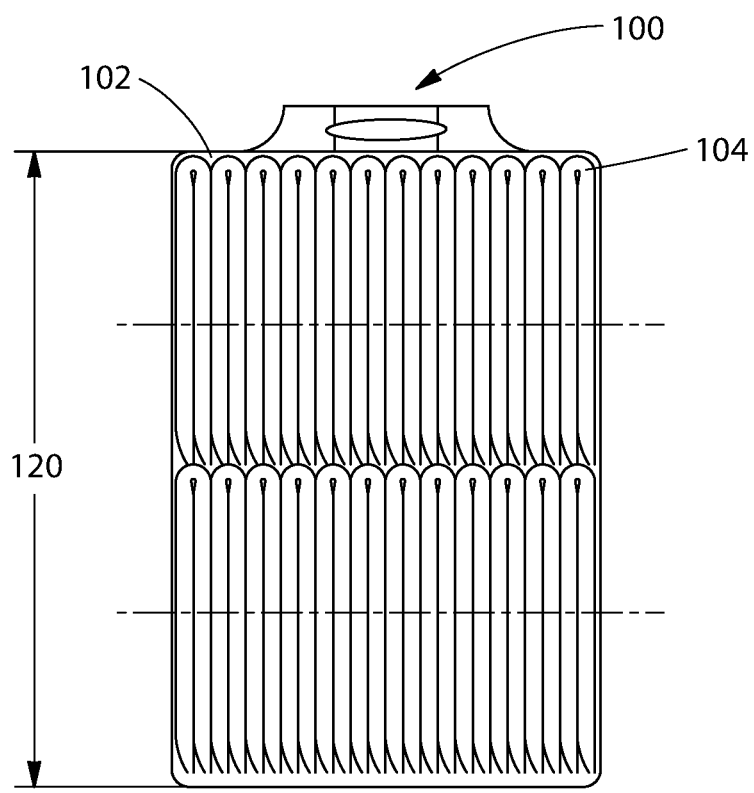
FIG. 5b is a side view of a package of absorbent articles in accordance with one embodiment showing the package height. The outer surface is illustrated as transparent for purposes of clarity.
Figure 5C:
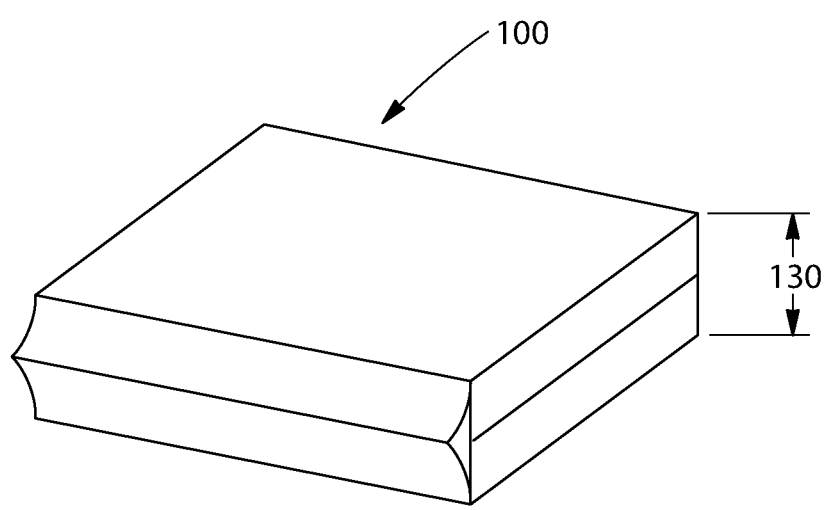
FIG. 5c is a perspective view of a package of absorbent articles in accordance with one embodiment showing the package depth.

As illustrated in FIG. 5a, package width 108 is defined as the maximum distance between the two highest bulging points along the same compression stack axis 110 of a diaper package. As illustrated in FIG. 5b, package height 120 is defined as the maximum distance between the bottom panel and highest point of the top panel. As illustrated in FIG. 5c, package depth 130 is defined as the maximum distance between the front and back panels of a diaper package.

Therefore, the Bag Utilization Factor can be determined by the following equation:

$$\text{Bag Utlization Factor } (m^2/pad/m) = \frac{\text{Surface Area of Package } (cm^2)/\text{Bag Count}}{\text{Folded Stack Length } (cm)} \div 100$$

Using the averages of Examples 1-5 from Table 2 below, the Bag Utilization Factor is determined as follows:

$$\text{Bag Utlization Factor (m}^2\text{/pad/m)} = \frac{\begin{array}{l}(16.3\,\text{cm} \times 40.1\,\text{cm} \times 2) + \\ (16.3\,\text{cm} \times 11.0\,\text{cm} \times 2) + \\ (40.1\,\text{cm} \times 11.0\,\text{cm} \times 2)/36\end{array}}{20.6\,\text{cm}} \div 100$$

$$= 3.436/100$$

$$= 0.034\,\text{m}^2\text{/pad/m}$$

In one embodiment, absorbent products according to the present disclosure may have a bag utilization factor of less than or equal to 0.030 m²/pad/m. In another embodiment, absorbent products may have a bag utilization factor of less than about 0.029 m²/pad/m. In another embodiment, absorbent products may have a bag utilization factor of from about 0.027 m²/pad/m to about 0.030 m²/pad/m.

In another embodiment, a Box Utilization Factor can also be determined by the following equation:

$$\text{Box Utlization Factor (m}^2\text{/pad/m)} = \frac{\text{Surface Area of Box (cm}^2\text{)/Box Count}}{\text{Folded Stack Length (cm)}} \div 100$$

In one embodiment, boxes containing absorbent products according to the present disclosure may have a box utilization factor of less than 0.0119 m²/pad/m. In another embodiment, boxes containing absorbent products according to the present disclosure may have a box utilization factor of from about 0.0090 m²/pad/m to about 0.0119 m²/pad/m.

FIGS. 8-15 describe a shipping optimization process for absorbent articles having a substantially airfelt free absorbent core. The overall shipping optimization process 400 according to the teachings of the disclosure includes five optimization procedures, the diaper optimization procedure 510, the bag optimization procedure 610, the box optimization procedure 710, the pallet optimization procedure 810, and the vehicle optimization procedure 910.

Figure 9:
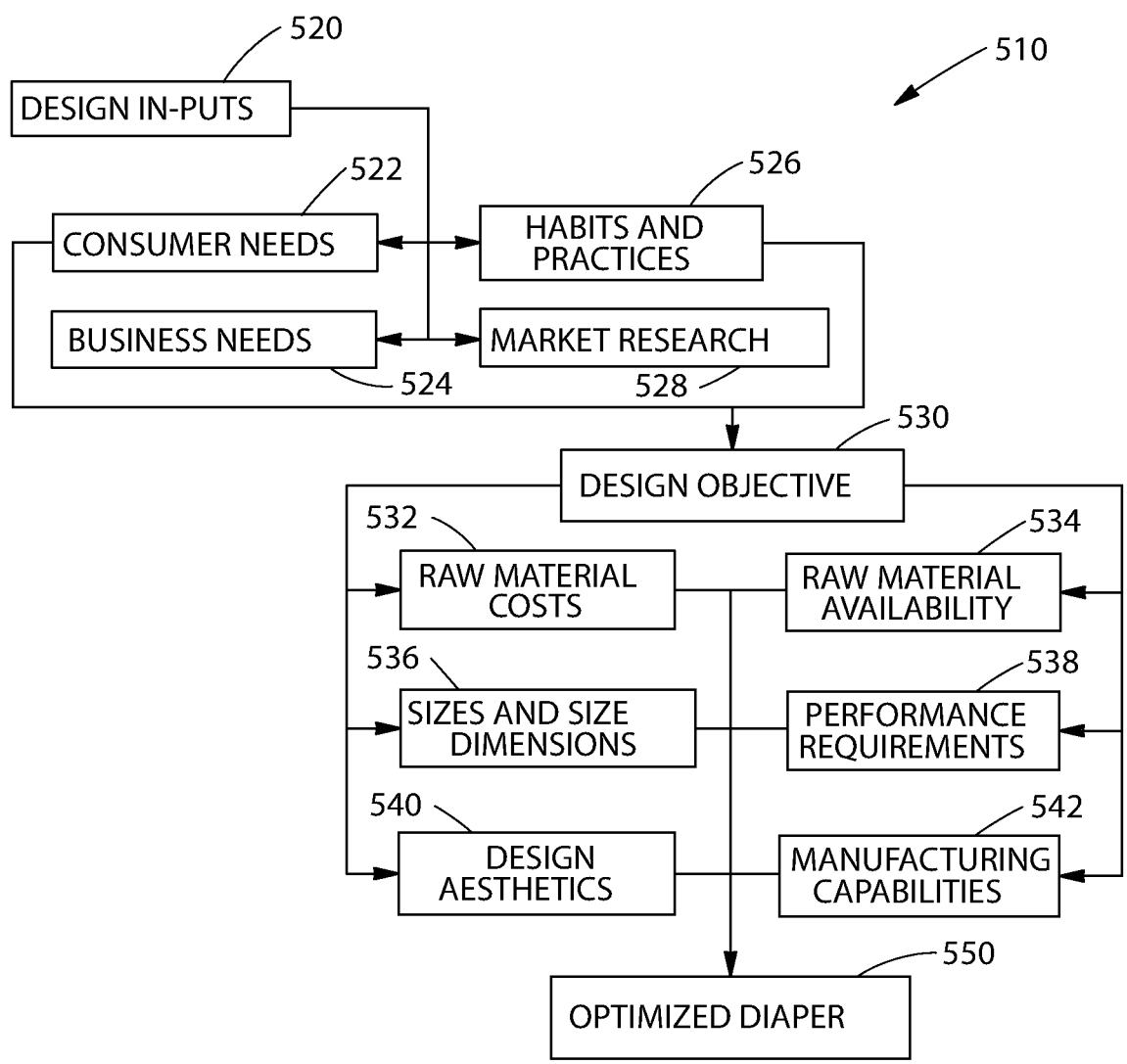
FIG. 9 is a logic diagram of the diaper optimization procedure of the optimization process of FIG. 4.

As shown in FIG. 9, the diaper optimization procedure 510 begins with a design input phase 520. The design input phase 520 includes gathering data regarding consumer needs 522, business needs 524, habits and practices 526, and market research 528. For example, consumer needs 522 may include data such as 1) absorbency requirements, 2) physiology of the consumer, 3) fluid absorbency rate, 4) fluid retention duration, 5) customer comfort, 6) weight of the diaper, etc. Business needs 524 may include data such as 1) capital equipment use, 2) gaps in the existing product line, 3) startup costs, 4) startup time, etc. Habits and practices 526 may include data such as 1) past consumer purchase practices, 2) change habits (including day and night frequencies), 3) when toilet training will start, etc. Market research 528 may include data such as 1) cross category purchases, 2) trade margins, 3) competitive marketing programs, etc. After completing the design inputs phase 520, the data collected is input into a design objective phase 530. After a basic design for the product is determined from the design inputs phase 520, several additional factors are considered to modify and engineer the product. For example, raw material costs 532 and raw material availability 534 may drive certain engineering choices to accomplish the design objectives 530. Moreover, the products sizes and dimensions 536 are determined based on the design inputs 520 data along with performance requirements 538. Ultimately the final optimized diaper 550 may be refined based on product aesthetics 540 and manufacturing capabilities 542. Normally products such as absorbent articles and diapers are not sold individually, but rather such absorbent articles are sold in packages containing a plurality of the absorbent articles. For example, smaller absorbent articles, such as infant diapers may be sold in packages of thirty or more diapers, while toddler training pants may be sold in packages of twelve to eighteen training pants. The number of absorbent articles placed in a package depends on several factors.

Figure 10:
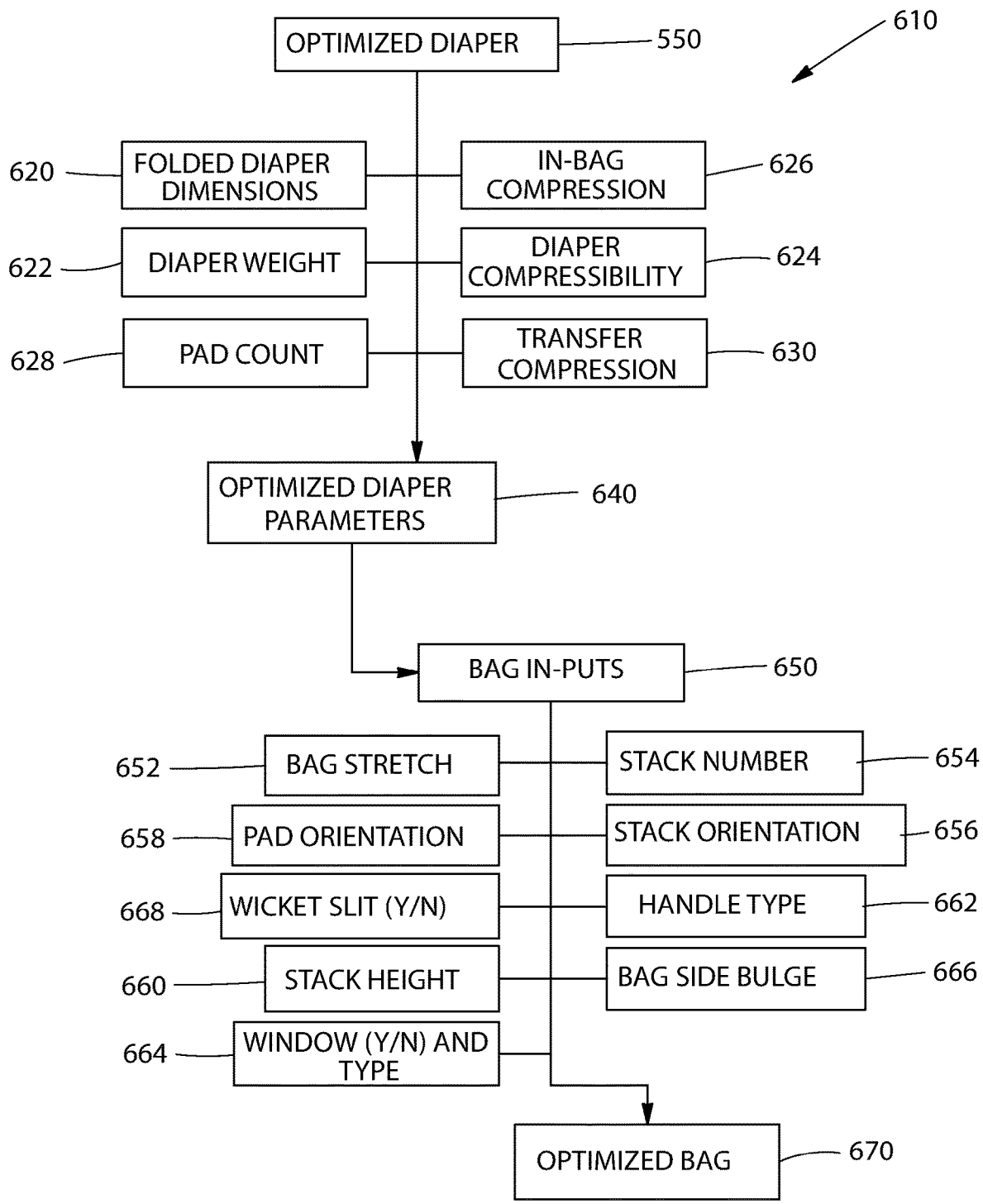
FIG. 10 is a logic diagram of the bag optimization procedure of the optimization process of FIG. 4.

As shown in FIG. 10, the optimized diaper 550 has certain characteristics based on the diaper design. For example, the optimized diaper 550 has certain folded dimensions 620, a certain weight 622, and a target compressibility range 624. For instance, new-born diapers (0-6 months) are expected to have a very soft backsheet feel. To prevent a reduction in backsheet softness, these diapers are normally compressed to between 30-38% within the product package, also known as in-bag compression 626, based on the number of pads 628 contained in the package. Baby diapers (6-12 months) and Toddlers (12-24+ months) do not have the same softness requirements and are normally compressed to between about 50 and 57% within the product package. Over-compression beyond this range will lead to stiffness in the diapers with air-felt cores, another undesired product negative. In order to package absorbent articles with this level of compression, the diapers must be transferred to the polybag or other package under a significant level of compression, known as transfer compression 630. Surprisingly, we have found that with larger size air-felt free diapers, the target compressibility range 624, can be increased to greater than about 58% without adversely affecting key consumer aesthetic attributes of the diaper (stiffness, softness, etc.). Once all the optimized diaper parameters are gathered at 640, data on the packaging is gathered at 650. Based on the optimized diaper parameters 640, certain materials may be selected for the package. Each material has different inherent physical characteristics, such as material stretch 652, material thickness, material weight, etc. Based on these material properties, a number of optimized diapers 654 may be selected for each individual package based on the packaging material, shipping and display limitations, orientation of the diapers 656, orientation of the pads in the diapers 658, and the height of the stack of diapers 660. Additional packing considerations include whether a handle should be included and if so, what type of handle 662 and whether a window 664 or a wicket slit 668 should be included in the package. The number of diapers and the type of material that comprises the container will determine how much side bulge 666 the completed package will have. Ultimately, an optimized package 670 is determined. The optimized package 670 will have certain physical characteristics and dimensions based on the type and number of diapers contained in the package.

Figure 11:
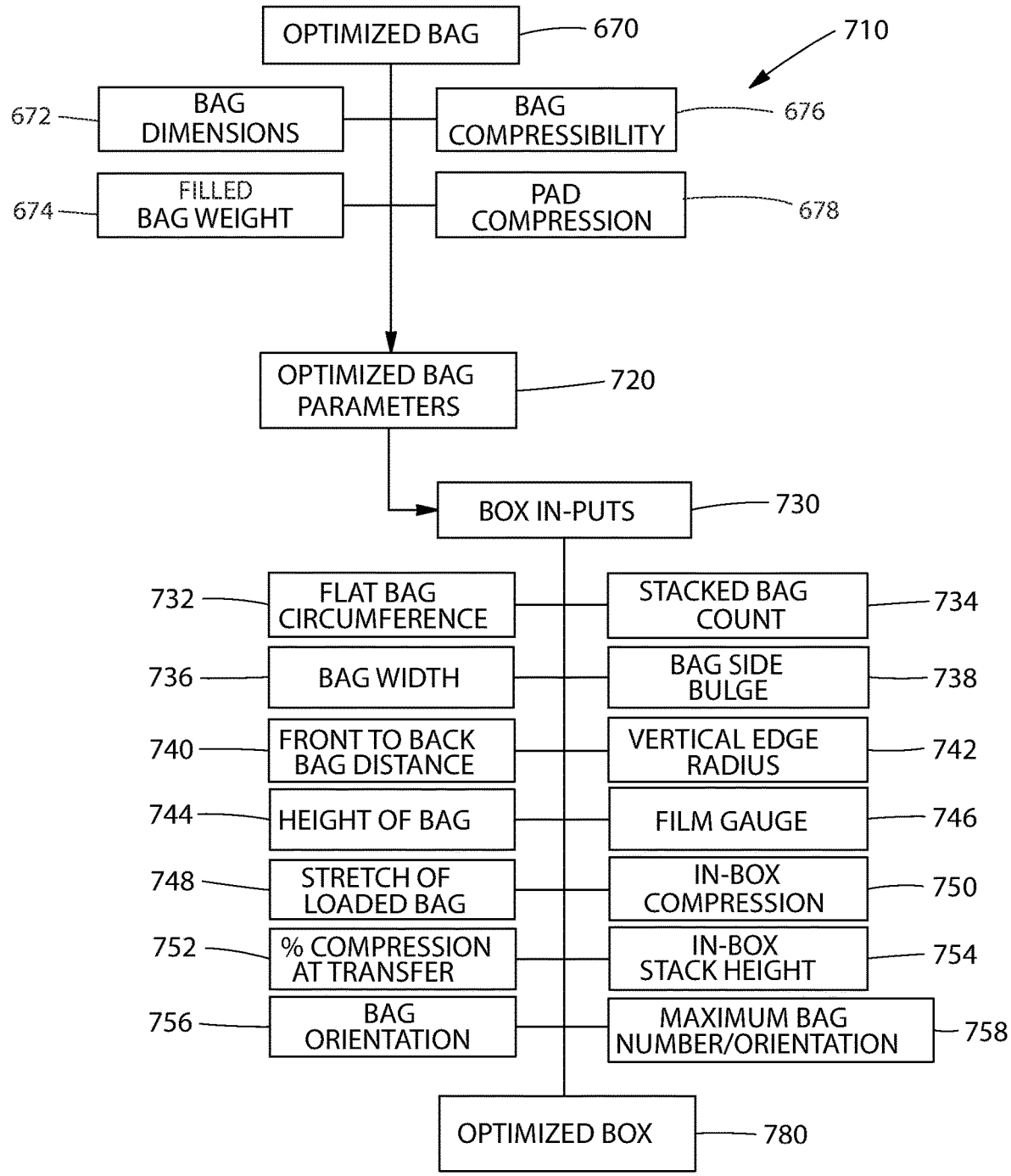
FIG. 11 is a logic diagram of the box optimization procedure of the optimization process of FIG. 4.
Figure 12A:
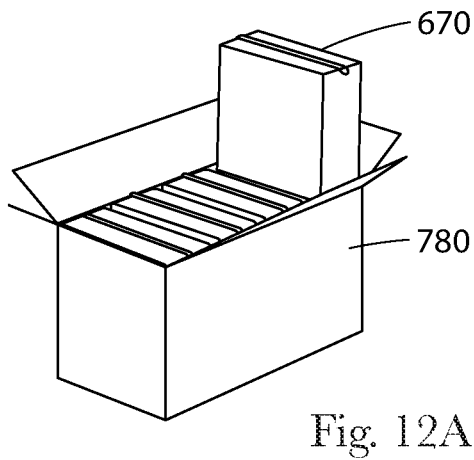
FIGS. 12a to 12f are perspective views of different box and bag orientations that may be considered during the box optimization procedure of FIG. 11.
Figure 12B:
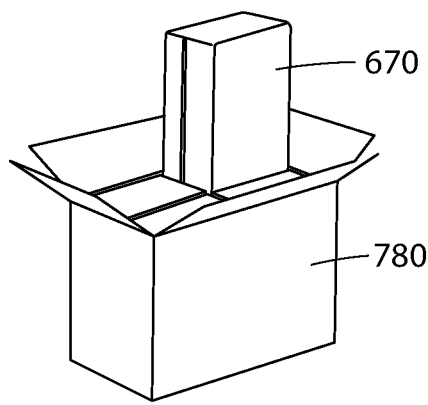
Figure 12C:
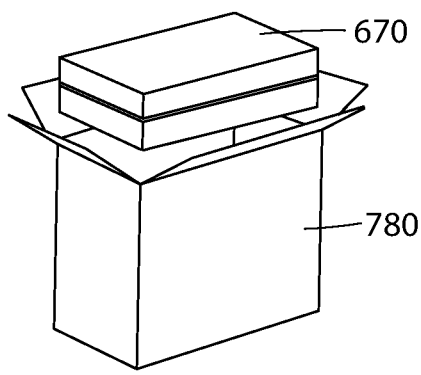
Figure 12D:
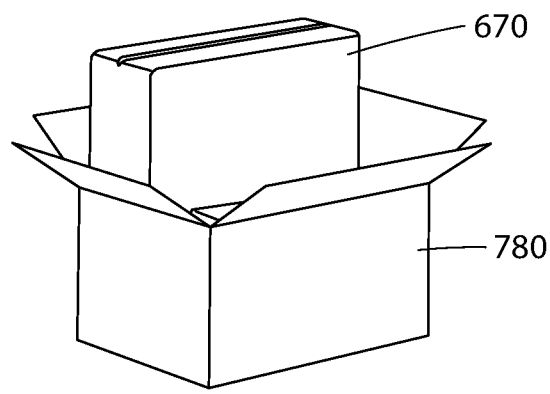
Figure 12E:
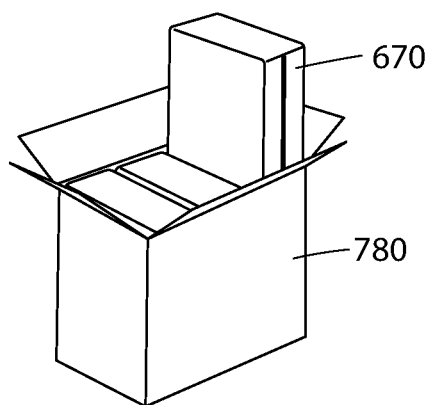
Figure 12F:
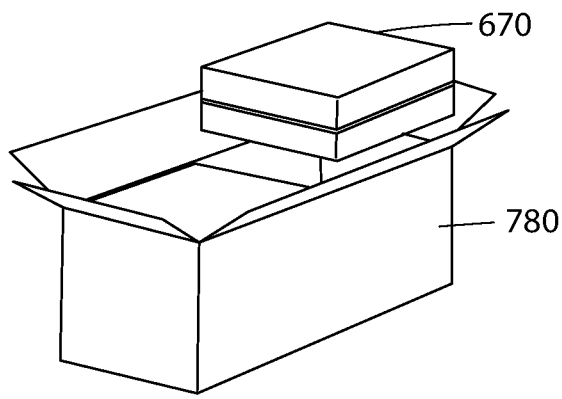

As shown in FIG. 11, the optimized package 670 has certain characteristics based on the package design. For example, the optimized package 670 has certain overall dimensions 672, including height, weight, and depth, a certain weight 674, and a package compressibility 676, which is dependent on, for example, the degree of compression 678 that the pads contained in the package are under. Typically a number of optimized packages 670 are shipped in larger containers or boxes 780. These larger containers or boxes 780 make loading and unloading of shipping vehicles more efficient. Once the optimized package 670 parameters are determined at 720, the larger container or box 780 may initially be sized based on the number of package 670 desired in each container or box 780. Once a general idea as to the number of packages 670 should be in each box 780 is determined at 734, physical data describing each package 670 is gathered. The data may include the package circumference 732, the package width 736, the package length 740, the package side bulge 738, the package edge radius 742, the package height 744, the film thickness or gauge 746, and the stretch of the loaded package 748. Each package 770 will also have a certain amount of in-box compression 750 when loaded and each stack of packages 670 will have an in-box height 754. Some of these factors will depend on package orientation 756.

As shown in FIG. 12, the packages 670 may be loaded in many different orientations within the box 780. The orientations shown in FIG. 12 are for illustration purposes only, other package 670 orientations are possible during the box 780 optimization process. Some exemplary package 670 orientations are a horizontal side oriented width-wise stack, as shown in the top left illustration; a horizontal side oriented length-wise stack, as shown in the top right illustration; a dual upright horizontal depth-wise stack, as shown in the middle left illustration; a flat vertical length-wise stack, as shown in the lower left illustration; an upright horizontal width-wise stack, as shown in the middle right illustration; and a dual flat vertical width-wise stack, as shown in the lower right illustration. Each loading configuration may result in a different shaped or dimensioned box 780. On the other hand, the loading orientation may be adapted to standard box 780 shapes and sizes. Each box 780 may have an ultimate weight capacity, based on the material and construction of the box 780, and a volume capacity. When optimizing loading of the box 480, the number and orientation of packages 670 is optimized based on the weight and volume capacity of the box 780.

Figure 13:
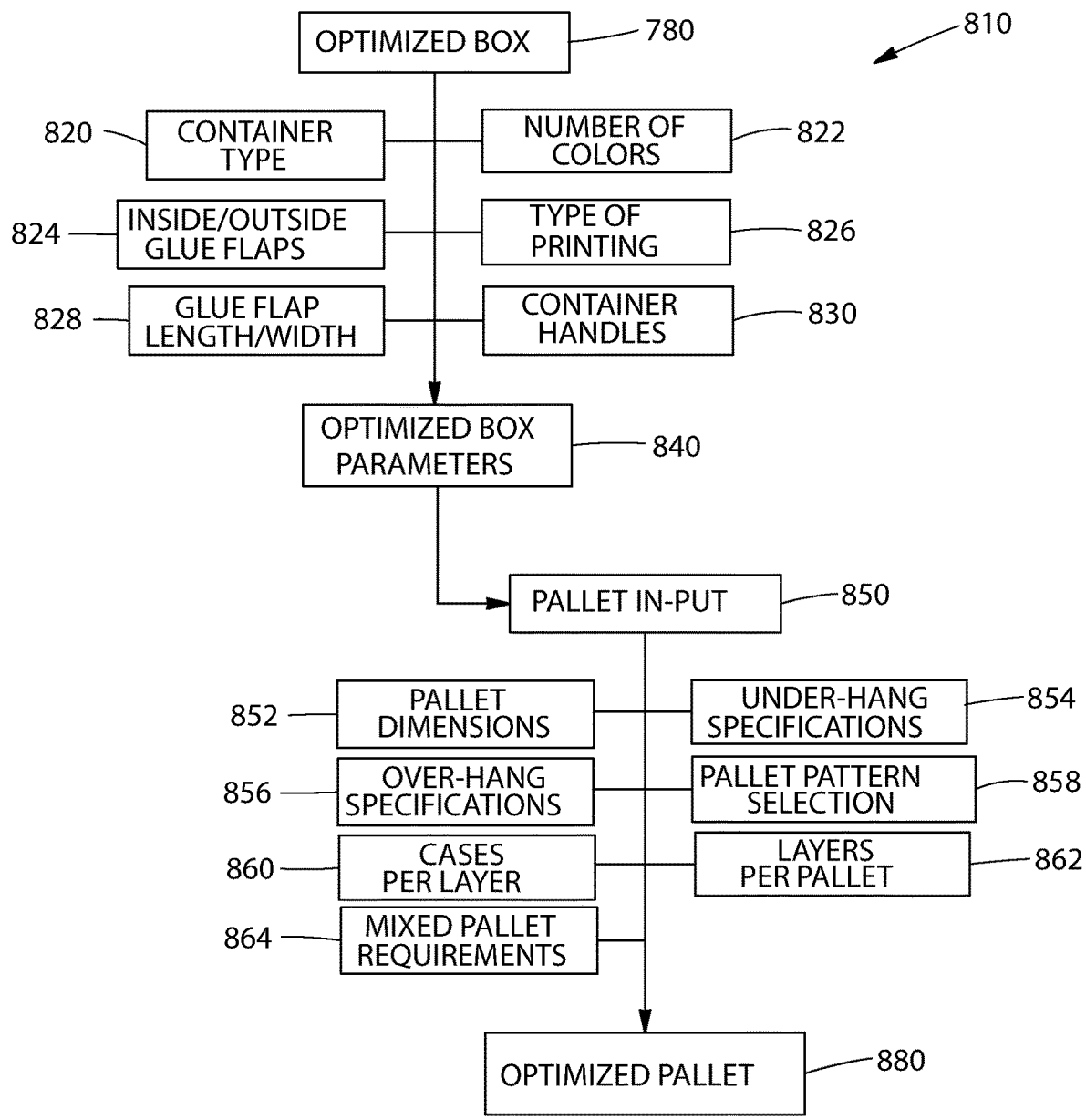
FIG. 13 is a logic diagram of the pallet optimization procedure of the optimization process of FIG. 8.

Once an optimal box design is determined, peripheral features may be included in the optimized box 780. For example, as shown in FIG. 13, the optimized box 780 may further include a container type 820, a color of a container 822, printing on the container 826, and handles on the container 830. Color and printing on the container may help readily identify each optimized box 780 as containing a certain absorbent product. The type and location of the flaps 828 and the type and location of adhesive 824 may also be determined Once the optimized box 780 is finalized, the box parameters may be determined at 840. The box 780 parameters are input into a pallet loading optimization process at 850.

A pallet (sometimes called a skid) is a flat transport structure that supports goods in a stable fashion while being lifted by a forklift, pallet jack, or other jacking device. A pallet is the foundation of a unit load design, which can be as simple as placing the goods on a pallet, and securing them with straps or stretch-wrapped plastic film, or as exotic as a ULD mini-container.

Containerization for transport has spurred the use of pallets because the containers have the clean, level surfaces needed for easy pallet movement. Most pallets can easily carry a load of 1,000 kg (about 2,000 lb). Pallets make it easy to move heavy stacks. Loads with pallets under them can be hauled by forklift trucks of different sizes, or even by hand-pumped and hand-drawn pallet jacks. Movement is easy on a wide, strong, flat floor, such as concrete. Organizations using standard pallets for loading and unloading can have much lower costs for handling and storage, with faster material movement than businesses that do not. The lack of a single international standard for pallets causes substantial continuing expense in international trade. A single standard is difficult because of the wide variety of needs a standard pallet would have to satisfy, such as passing doorways, fitting in standard containers, and bringing low labor costs. For example, organizations already handling large pallets often see no reason to pay the higher handling cost of using smaller pallets that can fit through doors.

The size, shape, and weight capacity of a given pallet may be determined in part by the shipping vehicle into which the pallet will be placed. Moreover, the volume capacity of a pallet is generally undetermined because pallets generally do not have side walls or tops. However, a volume capacity of a pallet can be determined based on a particular shipping vehicle. For example, if a particular shipping vehicle has an interior height of approximately 110 inches (e.g., a typical interior height of a semi trailer), then the combined height of the pallets and products cannot exceed 110 inches. Moreover, the combined height of the pallets must be less than 110 inches so that they can be inserted, stacked, and removed from the trailer using common loading and unloading techniques (e.g. using a forklift). Typical pallets are 5.75 inches high. Thus, if two levels of pallets are desired, each pallet can have a maximum product height of about 4 feet (48 inches). Typically, a semi-trailer is loaded with two rows of pallets, side by side. Semi-trailers are usually 8 ft, or 96 inches wide. Pallets may measure 3.3 by 4 ft (40×48 inches). If the rows of pallets are alternated so that the pallets inserted side by side have one 40 inch and one 48 inch side perpendicular to the length of the trailer, there will be a few inches of space between and on each side of the two pallets. This extra space also provides the room necessary for easy insertion and removal of the pallets. This alternating pallet configuration is also staggered from the front to the back of the trailer, thereby minimizing gaps between pallets and minimizing load shifting during transportation. A typical semi-trail can hold up to 60 pallets, 30 per layer, in this type of configuration. In addition, the area of a typical pallet may be approximately 13.2 square feet. By determining the maximum height of the pallet and products to be 4 feet when loaded in the vehicle, the volume capacity of each pallet in this example is approximately 52.8 cubic feet. In reality, each pallet must be designed to have 1-2 inches on underhang on each pallet to minimize product damage during shipment. Too much underhang will lead to unstable pallet loads and any amount of overhang will likely lead to product damage. If the desired underhang is subtracted from the previously calculated volume capacity of the pallet, a more accurate number for a true volume capacity for each pallet is about 52.4 ft$^3$.

As shown in FIG. 13, generally the pallet volume capacity may be determined by the pallet dimensions 852, under or over hang specifications 854, 856, pallet pattern selection 858, cases per pallet 860, layers per pallet 862, and mixed pallet requirements 864. The pallet weight capacity may be determined by the pallet material and the pallet construction. However, the pallet weight capacity is also dependent on the trailer weight capacity. For instance, if the trailer maximum legal weight capacity is about 50,000 lbs and there are 60 pallets contained within the trailer, each pallet would have a maximum load capacity of about 830 lbs. Each pallet weighs about 65 lbs, so the net load capacity of each pallet is about 765 lbs. Given each pallet has a maximum load capacity of about 765 lbs and a maximum volume capacity of about 52.4 ft$^3$, the maximum density of product and packages on each pallet would be approximately 14.6 lbs/ft$^3$. This number is significant in that it highlights that shipments of traditional air-felt absorbent products, especially diaper products, significantly underutilize the weight capacity of the most common form of product transportation, semi-trailers. Today's traditional air-felt absorbent article products, averaging a little under 9 lbs/ft3 have an average Load Factor of about 0.62 and a maximum Load Factor of about 0.70, while the substantially air-felt free absorbent article products may have an average Load Factor of about 0.82 and a minimum Load Factor of about 0.75. In one embodiment, the substantially air-felt free absorbent article products may have a Load Factor between about 0.75 and about 1.0, in another embodiment between about 0.77 and about 1.0, and in another embodiment between about 0.81 and about 0.95.

The Load Factor can be determined by the following equation:

Load Factor=(Weight of Trailer Load/Legal Trailer Weight Limit)/(Volume of Trailer Load/Volume Capacity of Trailer)

As a result, a significant savings in terms of logistics costs in getting these products from a manufacturing site through distribution and on to the store shelves is realized.

Figure 14:
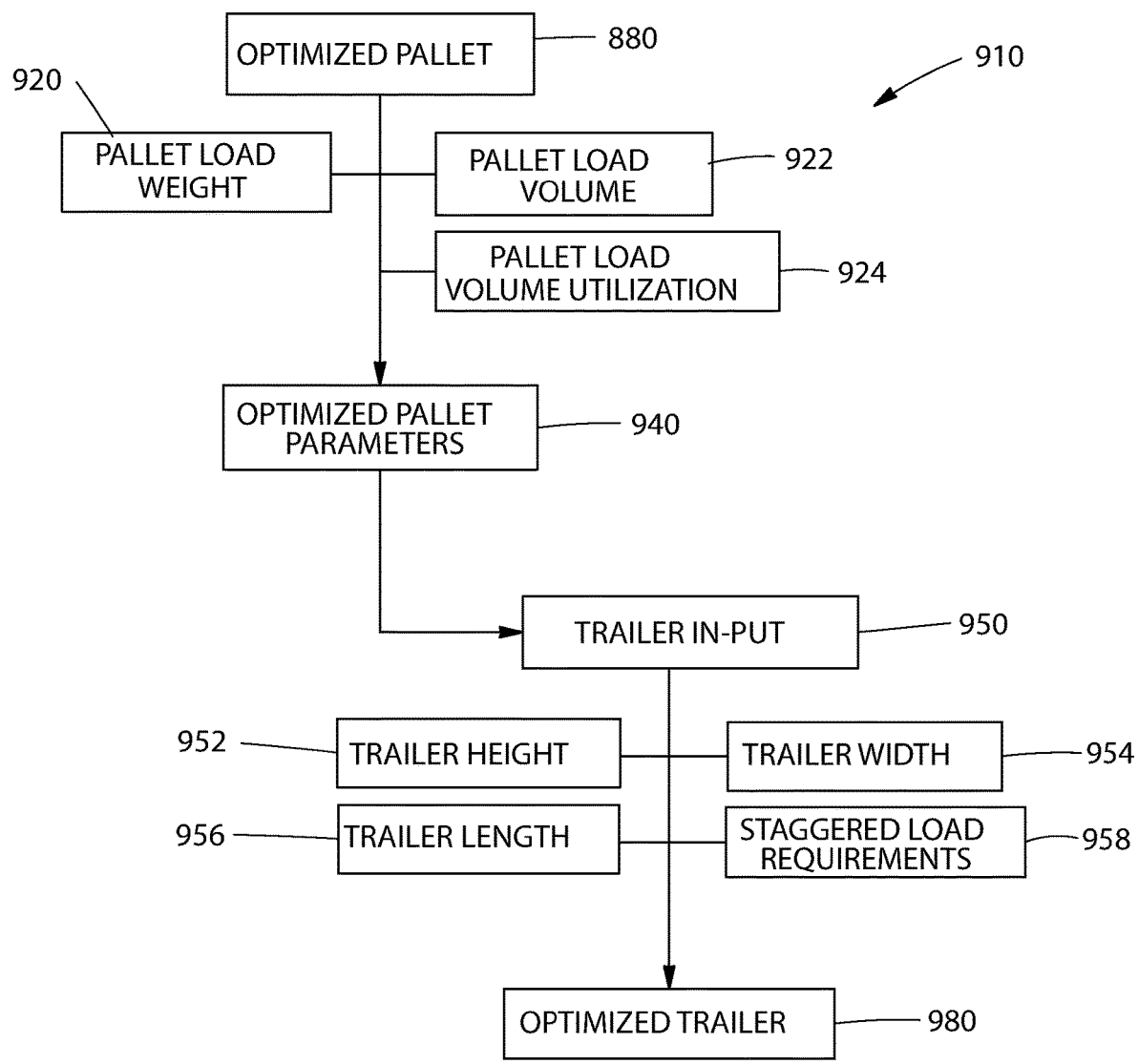
FIG. 14 is a logic diagram of the vehicle optimization procedure of the optimization process of FIG. 8.

As shown in FIG. 14 and indicated previously, the optimized pallet 880 will have certain physical characteristics useful in load planning of a transportation vehicle, such as a trailer. The optimized pallet 880 includes a loaded weight 920, a loaded volume 922 and a loaded volume utilization 924. These optimized pallet parameters 940 are used to create a load plan for the transportation vehicle at 950. The transportation vehicle includes certain physical transportation area dimensions, such as a height 952, a length 956, and a width 954 along with staggered load requirements 958. Once all the pallet and vehicle parameters are determined, the vehicle is loaded such that the optimized loaded vehicle 980 has a Load Factor of between 0.7 and 1.0. Again, this load factor assures the user that he/she is maximizing his/her transportation value.

In one embodiment, a pallet of absorbent products comprises a plurality of packages each having a plurality of disposable absorbent articles disposed within the interior space of the package, each of the disposable absorbent articles having a topsheet; a backsheet; a substantially cellulose free absorbent core located between the topsheet and the backsheet; a first waist region; a second waist region; a crotch region extending longitudinally between the first and second waist regions; and a fastening member extending laterally outward from the second waist region and adapted to releasably connect with a landing zone located in the first waist region; wherein the absorbent products arranged on the pallet exhibit a calculated Load Factor less than about 1.0, in another embodiment from about 0.7 to about 1.0.

In one embodiment, a shipping vehicle of absorbent products comprises a transportation area for receiving items to be transported, the vehicle having a maximum weight capacity for transporting items and a maximum volume capacity for transporting items; and a plurality of packages each having a plurality of disposable absorbent articles disposed within the interior space of the package, each of the disposable absorbent articles having a topsheet; a backsheet; a substantially cellulose free absorbent core located between the topsheet and the backsheet; a first waist region; a second waist region; a crotch region extending longitudinally between the first and second waist regions; and a fastening member extending laterally outward from the second waist region and adapted to releasably connect with a landing zone located in the first waist region; wherein the vehicle exhibits a calculated Load Factor of from about 0.7 to about 1.0, in another embodiment from about 0.75 to about 1.0.

Figure 15:
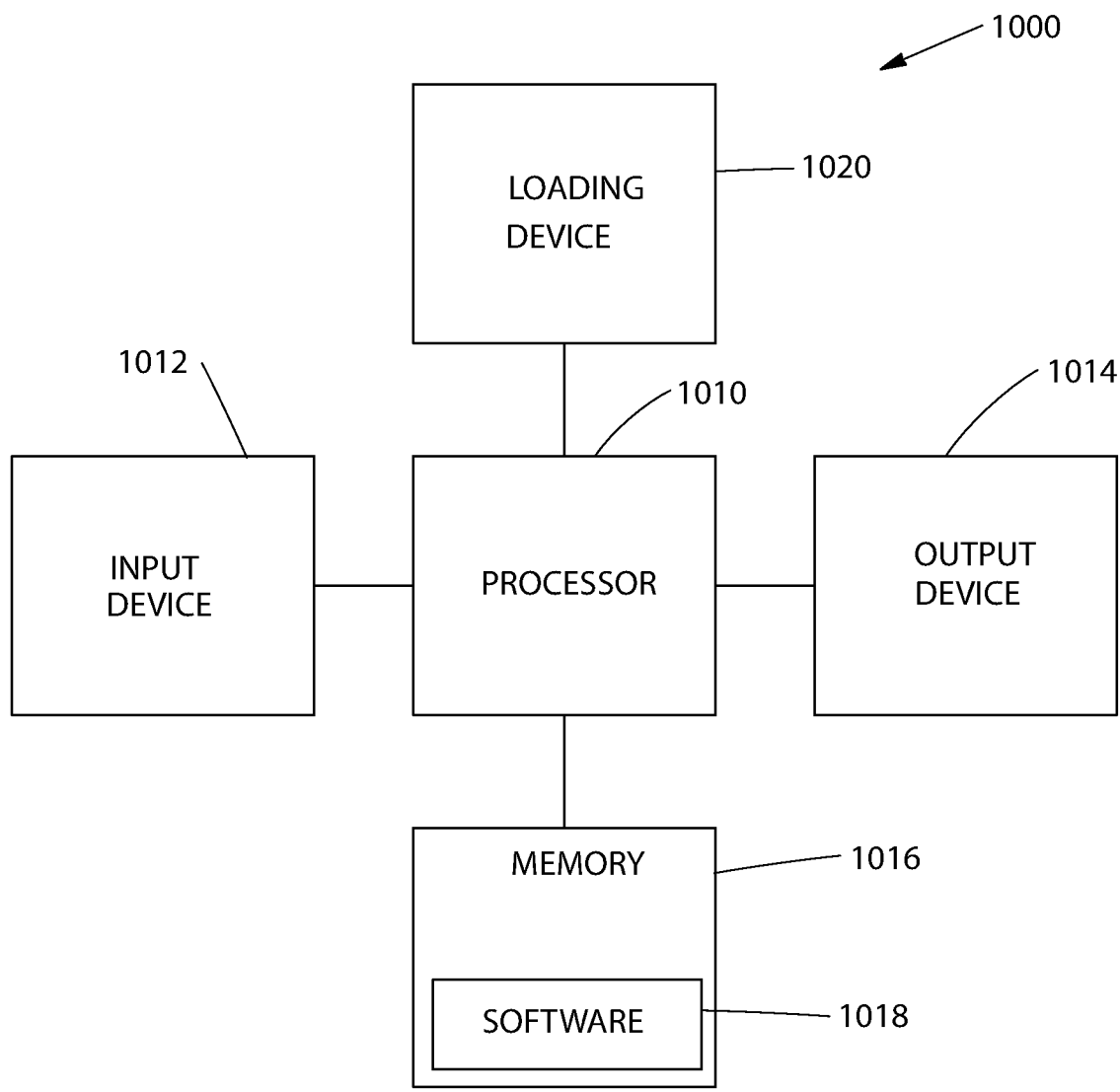
FIG. 15 is a schematic diagram of a load optimization system constructed in accordance with the teachings of the disclosure.
Figure 16:
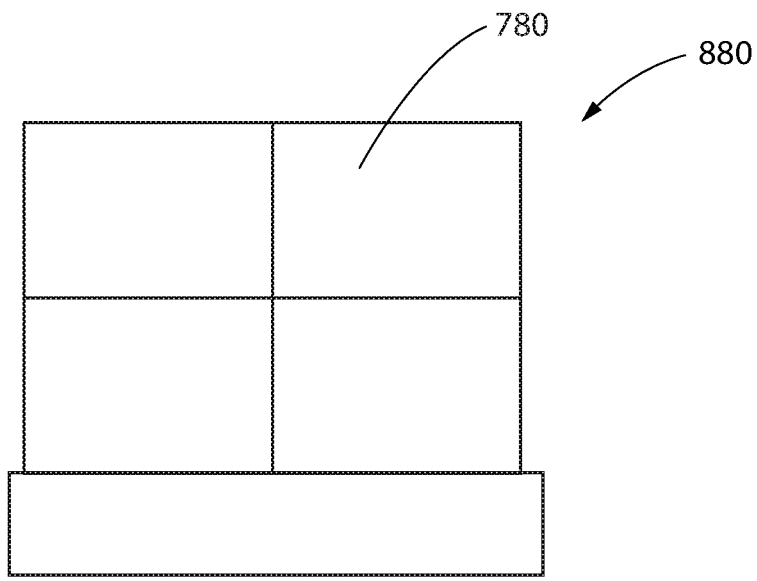
FIG. 16 is a front plan view of a pallet comprising containers or boxes.

FIG. 15 is a schematic diagram of a load planning system constructed in accordance with the teachings of the disclosure. The load planning system 1000 includes a processor 1010 operatively connected to an input device 1012, such as a computer keyboard, a computer mouse, a voice recognition system, a touchscreen, or any other type of input device, and an output device 1014, such as a computer monitor, a computer printer, a speaker, or any other type of output device. The processor 1010 is operatively coupled to a memory 1016. The memory 1016 may include software 1018 having one or more routines operable on the processor 1010. The software routines may perform the processes illustrated in FIGS. 8-15. The processor 1010 may also be connected to a loading device, such as an automatic loading system, or a display to instruct manual loaders. The software routines may run iteratively on the processor 1010 until the load factor is optimized for each of the packaging, the container, the pallet and the vehicle. Examples of container loading and cargo load planning software are MaxLoad Pro, commercially available from TOPS Engineering Corporation of Richardson, Tex. and CubeMaster, commercially available from Logen Solutions, Co. of Belmont, Calif.

EXAMPLES

The following Examples provide a comparison between diapers that are commercially available in the United States to diapers having optimized parameters according to the present disclosure. Tables 2-6 provide data for various diaper packages (folded stack length, in-bag stack height, and bag utilization factor) measured according to the Folded Stack Length Test and In-Bag Stack Height Test described in detail below.

TABLE 2

In-Bag Stack Height/Bag Utilization Factor Results for Sample Diaper Packages (Size 3)

| Example | Height (mm) | Width (mm) | Depth (mm) | Bag Count | Pad Count Per Stack | Child Wt. Range (kg) | Folded Stack Length (mm) | In-Bag Stack Ht (mm) | Bag Utilization Factor ($m^2$/pad/m) |
|---|---|---|---|---|---|---|---|---|---|
| 1. | 400 | 166 | 110 | 36 | 18 | 7-13 | 210 | 92 | 0.0340 |
| 2. | 401 | 163 | 110 | 36 | 18 | 7-13 | 206 | 91 | 0.0344 |
| 3. | 400 | 162 | 109 | 36 | 18 | 7-13 | 206 | 90 | 0.0340 |
| 4. | 402 | 162 | 110 | 36 | 18 | 7-13 | 204 | 90 | 0.0346 |
| 5. | 400 | 164 | 109 | 36 | 18 | 7-13 | 206 | 91 | 0.0343 |
| Avg. | | | | | | | 206 | 91 | 0.034 |
| 6. | 211 | 284 | 217 | 52 | 26 | 7-13 | 210 | 109 | 0.0306 |
| 7. | 216 | 289 | 220 | 52 | 26 | 7-13 | 209 | 111 | 0.0319 |
| 8. | 213 | 281 | 217 | 52 | 26 | 7-13 | 208 | 108 | 0.0309 |
| 9. | 213 | 285 | 218 | 52 | 26 | 7-13 | 210 | 110 | 0.0310 |

TABLE 2-continued

In-Bag Stack Height/Bag Utilization Factor Results for Sample Diaper Packages (Size 3)

| Example | Height (mm) | Width (mm) | Depth (mm) | Bag Count | Pad Count Per Stack | Child Wt. Range (kg) | Folded Stack Length (mm) | In-Bag Stack Ht (mm) | Bag Utilization Factor ($m^2$/pad/m) |
|---|---|---|---|---|---|---|---|---|---|
| 10. | 208 | 274 | 223 | 52 | 26 | 7-13 | 208 | 105 | 0.0304 |
| Avg. | | | | | | | 209 | 109 | 0.031 |
| 11. | 204 | 295 | 102 | 26 | 26 | 7-13 | 211 | 113 | 0.0405 |
| 12. | 203 | 293 | 102 | 26 | 26 | 7-13 | 210 | 113 | 0.0403 |
| 13. | 205 | 294 | 101 | 26 | 26 | 7-13 | 208 | 113 | 0.0409 |
| 14. | 204 | 294 | 104 | 26 | 26 | 7-13 | 208 | 113 | 0.0413 |
| 15. | 203 | 297 | 103 | 26 | 26 | 7-13 | 207 | 114 | 0.0415 |
| Avg. | | | | | | | 209 | 113 | 0.041 |
| 16. | 198 | 327 | 111 | 38 | 38 | 7-13 | 200 | 86 | 0.0324 |
| 17. | 197 | 328 | 111 | 38 | 38 | 7-13 | 205 | 86 | 0.0316 |
| 18. | 189 | 327 | 111 | 38 | 38 | 7-13 | 196 | 86 | 0.0320 |
| 19. | 187 | 329 | 112 | 38 | 38 | 7-13 | 196 | 87 | 0.0320 |
| 20. | 194 | 330 | 113 | 38 | 38 | 7-13 | 204 | 87 | 0.0318 |
| 21. | 193 | 334 | 114 | 38 | 38 | 7-13 | 205 | 88 | 0.0320 |
| Avg. | | | | | | | 201 | 87 | 0.032 |
| 22. | 203 | 229 | 114 | 31 | 31 | 7-13 | 205 | 74 | 0.0301 |
| 23. | 202 | 229 | 114 | 31 | 31 | 7-13 | 208 | 74 | 0.0296 |
| 24. | 204 | 230 | 112 | 31 | 31 | 7-13 | 207 | 74 | 0.0298 |
| 25. | 204 | 226 | 112 | 31 | 31 | 7-13 | 205 | 73 | 0.0297 |
| 26. | 204 | 226 | 113 | 31 | 31 | 7-13 | 206 | 73 | 0.0297 |
| Avg. | | | | | | | 206 | 74 | 0.030 |
| 27. | 393 | 203 | 113 | 52 | 26 | 7-13 | 206 | 78 | 0.0275 |
| 28. | 396 | 209 | 111 | 52 | 26 | 7-13 | 206 | 80 | 0.0280 |
| 29. | 392 | 207 | 110 | 52 | 26 | 7-13 | 204 | 80 | 0.0277 |
| 30. | 391 | 206 | 112 | 52 | 26 | 7-13 | 202 | 79 | 0.0281 |
| 31. | 392 | 207 | 110 | 52 | 26 | 7-13 | 204 | 80 | 0.0277 |
| Avg. | | | | | | | 204 | 79 | 0.028 |

Examples 1-5 are commercially available airfelt diapers sold by Kimberly-Clark Corporation under the trademark HUGGIES SNUG & DRY (size 3; bag count 36; Lot #'s UT915306F 10:09; UT915306F 09:50; UT916806B 06:17; UT915306F 09:50; and UT9168068 06:17, respectively).

Examples 6-10 are commercially available airfelt diapers sold by Kimberly-Clark Corporation under the trademark HUGGIES LITTLE MOVERS (size 3; bag count 52; Lot #'s UT815001B 22:24; BI913412B 00:20; BI913412B 00:20; BI913412B 00:19; and BI913412B 00:20, respectively).

Examples 11-15 are commercially available airfelt diapers sold by Kimberly-Clark Corporation under the trademark HUGGIES PURE & NATURAL (size 3; bag count 26; Lot # BI914617B 23:58—Ex. 11 and 12; BI920317B 06:00—Ex. 13; and BI920317B 01:19—Ex. 14 and 15).

Examples 16-21 are commercially available airfelt diapers sold by The Procter & Gamble Company under the trademark PAMPERS CRUISERS (size 3; bag count 76; Lot #'s 9154U01142 02:35 15837—Ex. 16 and 17; 9192U01142 09:41 38287—Ex. 18 and 19; and 9095U01142 11:03 25875—Ex. 20 and 21).

Examples 22-26 are embodiments of absorbent products in accordance with the present disclosure (size 3; bag count 31; Lot #'s 9242U01762X1028; 9242U01762X1009—Ex. 23-26).

Examples 27-31 are embodiments of absorbent products in accordance with the present disclosure (size 3; bag count 52; Lot #'s 9242U01762X1251—Ex. 27 and 28 and 9242U011762X1317—Ex. 29-31).

TABLE 3

In-Bag Stack Height/Bag Utilization Factor Results for Sample Diaper Packages (Size 4)

| Example | Height (mm) | Width (mm) | Depth (mm) | Bag Count | Pad Count Per Stack | Child Wt. Range (kg) | Folded Stack Length (mm) | In-Bag Stack Ht (mm) | Bag Utilization Factor ($m^2$/pad/m) |
|---|---|---|---|---|---|---|---|---|---|
| 32. | 230 | 262 | 116 | 31 | 31 | 10-17 | 228 | 85 | 0.0332 |
| 33. | 219 | 254 | 118 | 31 | 31 | 10-17 | 226 | 82 | 0.0318 |
| 34. | 222 | 267 | 116 | 31 | 31 | 10-17 | 222 | 86 | 0.0337 |
| 35. | 230 | 262 | 118 | 31 | 31 | 10-17 | 227 | 85 | 0.0336 |
| 36. | 221 | 261 | 116 | 31 | 31 | 10-17 | 219 | 84 | 0.0335 |
| Avg. | | | | | | | 224 | 84 | 0.033 |
| 37. | 212 | 340 | 220 | 32 | 32 | 10-17 | 218 | 106 | 0.0555 |
| 38. | 220 | 336 | 222 | 32 | 32 | 10-17 | 223 | 105 | 0.0553 |
| 39. | 215 | 339 | 224 | 32 | 32 | 10-17 | 221 | 106 | 0.0557 |
| 40. | 209 | 337 | 218 | 32 | 32 | 10-17 | 215 | 105 | 0.0551 |
| 41. | 211 | 337 | 219 | 32 | 32 | 10-17 | 215 | 105 | 0.0556 |
| Avg. | | | | | | | 218 | 106 | 0.055 |
| 42. | 218 | 255 | 109 | 23 | 23 | 10-17 | 226 | 111 | 0.0412 |
| 43. | 217 | 258 | 108 | 23 | 23 | 10-17 | 227 | 112 | 0.0411 |

TABLE 3-continued

In-Bag Stack Height/Bag Utilization Factor Results for Sample Diaper Packages (Size 4)

| Example | Height (mm) | Width (mm) | Depth (mm) | Bag Count | Pad Count Per Stack | Child Wt. Range (kg) | Folded Stack Length (mm) | In-Bag Stack Ht (mm) | Bag Utilization Factor ($m^2$/pad/m) |
|---|---|---|---|---|---|---|---|---|---|
| 44. | 216 | 255 | 109 | 23 | 23 | 10-17 | 222 | 111 | 0.0417 |
| 45. | 217 | 257 | 108 | 23 | 23 | 10-17 | 226 | 112 | 0.0411 |
| 46. | 216 | 254 | 108 | 23 | 23 | 10-17 | 226 | 110 | 0.0406 |
| Avg. | | | | | | | 225 | 111 | 0.041 |
| 47. | 218 | 233 | 110 | 27 | 27 | 10-17 | 225 | 86 | 0.0331 |
| 48. | 218 | 233 | 111 | 27 | 27 | 10-17 | 222 | 86 | 0.0337 |
| 49. | 218 | 232 | 111 | 27 | 27 | 10-17 | 225 | 86 | 0.0337 |
| 50. | 217 | 239 | 111 | 27 | 27 | 10-17 | 219 | 89 | 0.0347 |
| 51. | 219 | 233 | 114 | 27 | 27 | 10-17 | 221 | 86 | 0.0344 |
| Avg. | | | | | | | 222 | 87 | 0.034 |
| 52. | 217 | 211 | 112 | 27 | 27 | 10-17 | 220 | 78 | 0.0316 |
| 53. | 216 | 208 | 112 | 27 | 27 | 10-17 | 216 | 77 | 0.0317 |
| 54. | 216 | 210 | 112 | 27 | 27 | 10-17 | 220 | 78 | 0.0313 |
| 55. | 216 | 209 | 112 | 27 | 27 | 10-17 | 220 | 77 | 0.0312 |
| 56. | 212 | 212 | 112 | 27 | 27 | 10-17 | 219 | 79 | 0.0313 |
| Avg. | | | | | | | 219 | 78 | 0.031 |
| 57. | 212 | 344 | 121 | 46 | 46 | 10-17 | 221 | 75 | 0.0276 |
| 58. | 213 | 344 | 117 | 46 | 46 | 10-17 | 220 | 75 | 0.0274 |
| 59. | 213 | 345 | 120 | 46 | 46 | 10-17 | 220 | 75 | 0.0278 |
| 60. | 214 | 349 | 118 | 46 | 46 | 10-17 | 221 | 76 | 0.0278 |
| 61. | 211 | 348 | 119 | 46 | 46 | 10-17 | 222 | 76 | 0.0274 |
| Avg. | | | | | | | 221 | 75 | 0.028 |

Examples 32-36 are commercially available airfelt diapers sold by Kimberly-Clark Corporation under the trademark HUGGIES SNUG & DRY (size 4; bag count 31; Lot #'s PA913908B 20:06; BI917716B 22:41; WP 920310 F; PA913908B 20:05; and WP 920310 F, respectively).

Examples 37-41 are commercially available airfelt diapers sold by Kimberly-Clark Corporation under the trademark HUGGIES LITTLE MOVERS (size 4; bag count 64; Lot #'s UT916502B 2049#9917; BI916812X 10:15 82616; BI919112X 11:16 331403; UT917102F 10:01 4548; and UT917102F 09:57, respectively).

Examples 42-46 are commercially available airfelt diapers sold by Kimberly-Clark Corporation under the trademark HUGGIES PURE & NATURAL (size 4; bag count 23; Lot #'s BI911212B 21:24—Ex. 42-44 and BI911212B 21:18—Ex. 45 and 46).

Examples 47-51 are commercially available airfelt diapers sold by The Procter & Gamble Company under the trademark PAMPERS CRUISERS (size 4; bag count 27; Lot #'s 9200 U01129 21:15—Ex. 47-49; 9194U01129 11:46; and 9214 U01754 19:30, respectively).

Examples 52-56 are embodiments of absorbent products in accordance with the present disclosure (size 4; bag count 27; Lot #'s 924762U01762X1755—Ex. 52, 53 and 55; and 924762U01762X1754—Ex. 54 and 56).

Examples 57-61 are embodiments of absorbent products in accordance with the present disclosure (size 4; bag count 46; Lot #9247U01762X10:36).

TABLE 4

In-Bag Stack Height/Bag Utilization Factor Results for Sample Diaper Packages (Size 5)

| Example | Height (mm) | Width (mm) | Depth (mm) | Bag Count | Pad Count Per Stack | Child Wt. Range (kg) | Folded Stack Length (mm) | In-Bag Stack Ht (mm) | Bag Utilization Factor ($m^2$/pad/m) |
|---|---|---|---|---|---|---|---|---|---|
| 62. | 235 | 304 | 120 | 35 | 35 | 12+ | 232 | 87 | 0.0335 |
| 63. | 234 | 304 | 121 | 35 | 35 | 12+ | 229 | 87 | 0.0340 |
| 64. | 234 | 295 | 119 | 35 | 35 | 12+ | 236 | 84 | 0.0320 |
| 65. | 235 | 294 | 118 | 35 | 35 | 12+ | 230 | 84 | 0.0327 |
| 66. | 234 | 302 | 122 | 35 | 35 | 12+ | 232 | 86 | 0.0335 |
| 67. | 235 | 305 | 121 | 35 | 35 | 12+ | 233 | 87 | 0.0336 |
| Avg. | | | | | | | 232 | 86 | 0.033 |
| 68. | 224 | 256 | 111 | 23 | 23 | 12+ | 230 | 111 | 0.0418 |
| 69. | 230 | 258 | 112 | 23 | 23 | 12+ | 231 | 112 | 0.0429 |
| 70. | 221 | 254 | 111 | 23 | 23 | 12+ | 223 | 110 | 0.0424 |
| 71. | 223 | 255 | 111 | 23 | 23 | 12+ | 223 | 111 | 0.0429 |
| 72. | 224 | 253 | 111 | 23 | 23 | 12+ | 226 | 110 | 0.0422 |
| Avg. | | | | | | | 227 | 111 | 0.042 |
| 73. | 215 | 261 | 104 | 20 | 20 | 12+ | 221 | 131 | 0.0477 |
| 74. | 217 | 264 | 102 | 20 | 20 | 12+ | 221 | 132 | 0.0483 |

TABLE 4-continued

In-Bag Stack Height/Bag Utilization Factor Results for Sample Diaper Packages (Size 5)

| Example | Height (mm) | Width (mm) | Depth (mm) | Bag Count | Pad Count Per Stack | Child Wt. Range (kg) | Folded Stack Length (mm) | In-Bag Stack Ht (mm) | Bag Utilization Factor ($m^2$/pad/m) |
|---|---|---|---|---|---|---|---|---|---|
| 75. | 215 | 261 | 102 | 20 | 20 | 12+ | 224 | 130 | 0.0468 |
| 76. | 222 | 269 | 95 | 20 | 20 | 12+ | 227 | 134 | 0.0469 |
| 77. | 214 | 262 | 104 | 20 | 20 | 12+ | 223 | 131 | 0.0473 |
| Avg. | | | | | | | 223 | 132 | 0.047 |
| 78. | 212 | 268 | 117 | 28 | 28 | 12+ | 220 | 96 | 0.0367 |
| 79. | 211 | 269 | 118 | 28 | 28 | 12+ | 218 | 96 | 0.0372 |
| 80. | 210 | 267 | 118 | 28 | 28 | 12+ | 220 | 95 | 0.0365 |
| 81. | 212 | 270 | 117 | 28 | 28 | 12+ | 219 | 96 | 0.0371 |
| 82. | 212 | 271 | 120 | 28 | 28 | 12+ | 221 | 97 | 0.0373 |
| 83. | 211 | 271 | 121 | 28 | 28 | 12+ | 220 | 97 | 0.0375 |
| Avg. | | | | | | | 220 | 96 | 0.037 |
| 84. | 214 | 302 | 120 | 40 | 40 | 12+ | 223 | 76 | 0.0284 |
| 85. | 213 | 304 | 118 | 40 | 40 | 12+ | 226 | 76 | 0.0278 |
| 86. | 216 | 304 | 120 | 40 | 40 | 12+ | 225 | 76 | 0.0285 |
| 87. | 216 | 302 | 119 | 40 | 40 | 12+ | 225 | 76 | 0.0282 |
| 88. | 216 | 304 | 118 | 40 | 40 | 12+ | 222 | 76 | 0.0286 |
| Avg. | | | | | | | 224 | 76 | 0.028 |

Examples 62-67 are commercially available airfelt diapers sold by Kimberly-Clark Corporation under the trademark HUGGIES SNUG & DRY (size 5; bag count 35; Lot #'s PA919002B 04:11—Ex. 62 and 63; BI907015X 02:03 16118—Ex. 64 and 65; and PA915502F 17:00—Ex. 66 and 67).

Examples 68-72 are commercially available airfelt diapers sold by Kimberly-Clark Corporation under the trademark HUGGIES LITTLE MOVERS (size 5; bag count 23; Lot #'s PA914807X 17:15; PA914907X 02:04; and PA917707B 04:55—Ex. 70-72, respectively).

Examples 73-77 are commercially available airfelt diapers sold by Kimberly-Clark Corporation under the trademark HUGGIES PURE & NATURAL (size 5; bag count 20; Lot #'s UT918102F 16:33—Ex. 73-75; UT907802F 14:11; and UT918102F 14:45, respectively).

Examples 78-83 are commercially available airfelt diapers sold by The Procter & Gamble Company under the trademark PAMPERS CRUISERS (size 5; bag count 56; Lot #'s 9208U01130 08:07 02501—Ex. 78-81 and 9292U01130 21:12 46676—Ex. 82 and 83).

Examples 84-88 are embodiments of absorbent products in accordance with the present disclosure (size 5; bag count 40; Lot #9244U01762X1504).

TABLE 5

In-Bag Stack Height/Bag Utilization Factor Results for Sample Diaper Packages (Size 6)

| Example | Height (mm) | Width (mm) | Depth (mm) | Bag Count | Pad Count Per Stack | Child Wt. Range (kg) | Folded Stack Length (mm) | In-Bag Stack Ht (mm) | Bag Utilization Factor ($m^2$/pad/m) |
|---|---|---|---|---|---|---|---|---|---|
| 89. | 233 | 253 | 218 | 40 | 20 | 16+ | 233 | 127 | 0.0354 |
| 90. | 241 | 252 | 216 | 40 | 20 | 16+ | 235 | 126 | 0.0356 |
| 91. | 227 | 259 | 223 | 40 | 20 | 16+ | 233 | 130 | 0.0359 |
| 92. | 232 | 256 | 212 | 40 | 20 | 16+ | 239 | 128 | 0.0341 |
| 93. | 227 | 261 | 217 | 40 | 20 | 16+ | 237 | 131 | 0.0348 |
| Avg. | | | | | | | 235 | 128 | 0.035 |
| 94. | 237 | 219 | 108 | 20 | 20 | 16+ | 238 | 110 | 0.0425 |
| 95. | 235 | 220 | 108 | 20 | 20 | 16+ | 240 | 110 | 0.0420 |
| 96. | 233 | 220 | 110 | 20 | 20 | 16+ | 235 | 110 | 0.0430 |
| 97. | 237 | 217 | 111 | 20 | 20 | 16+ | 238 | 109 | 0.0428 |
| 98. | 232 | 219 | 111 | 20 | 20 | 16+ | 237 | 110 | 0.0426 |
| Avg. | | | | | | | 238 | 110 | 0.043 |
| 99. | 188 | 228 | 115 | 20 | 20 | 16+ | 235 | 114 | 0.0386 |
| 100. | 189 | 232 | 113 | 20 | 20 | 16+ | 233 | 116 | 0.0392 |
| 101. | 192 | 232 | 114 | 20 | 20 | 16+ | 235 | 116 | 0.0395 |
| 102. | 192 | 234 | 116 | 20 | 20 | 16+ | 235 | 117 | 0.0401 |
| 103. | 192 | 231 | 115 | 20 | 20 | 16+ | 235 | 116 | 0.0396 |
| Avg. | | | | | | | 235 | 116 | 0.039 |

Examples 89-93 are commercially available airfelt diapers sold by Kimberly-Clark Corporation under the trademark HUGGIES SNUG & DRY (size 6; bag count 40; Lot #'s PA901405B 03:52; PA901405B 03:54; WP 823109F; PA8142055 15:17; and PA901505F 14:41, respectively).

Examples 94-98 are commercially available airfelt diapers sold by Kimberly-Clark Corporation under the trademark HUGGIES LITTLE MOVERS (size 6; bag count 34; Lot #'s PA913107X 11:39; PA913107X 11:37; PA913207X 01:32; PA919007F 10:19; and PA910207X 23:21, respectively).

Examples 99-103 are commercially available airfelt diapers sold by The Procter & Gamble Company under the trademark PAMPERS CRUISERS (size 6; bag count 20; Lot #'s 9141U017642235 and 9155U017641647).

TABLE 6

In-Bag Stack Height/Bag Utilization Factor Results for Sample Diaper Packages (Training Pants)

| Example | Height (mm) | Width (mm) | Depth (mm) | Bag Count | Pad Count Per Stack | Child Wt. Range (kg) | Folded Stack Length (mm) | In-Bag Stack Ht (mm) | Bag Utilization Factor ($m^2$/pad/m) |
|---|---|---|---|---|---|---|---|---|---|
| 104. | 272 | 249 | 125 | 27 | 27 | 17-29 | 274 | 92 | 0.0359 |
| 105. | 277 | 248 | 123 | 27 | 27 | 17-29 | 275 | 92 | 0.0359 |
| 106. | 276 | 258 | 117 | 27 | 27 | 17-29 | 274 | 96 | 0.0361 |
| 107. | 275 | 256 | 117 | 27 | 27 | 17-29 | 278 | 95 | 0.0353 |
| 108. | 272 | 246 | 125 | 27 | 27 | 17-29 | 272 | 91 | 0.0359 |
| Avg. | | | | | | | 272 | 93 | 0.036 |
| 109. | 294 | 205 | 130 | 21 | 21 | 27-57+ | 293 | 98 | 0.0407 |
| 110. | 295 | 206 | 129 | 21 | 21 | 27-57+ | 290 | 98 | 0.0412 |
| 111. | 288 | 209 | 129 | 21 | 21 | 27-57+ | 286 | 100 | 0.0414 |
| 112. | 291 | 205 | 129 | 21 | 21 | 27-57+ | 287 | 98 | 0.0410 |
| 113. | 286 | 209 | 130 | 21 | 21 | 27-57+ | 286 | 100 | 0.0413 |
| Avg. | | | | | | | 288 | 98 | 0.041 |
| 114. | 266 | 166 | 124 | 15 | 15 | 17-29 | 268 | 111 | 0.0486 |
| 115. | 268 | 169 | 121 | 15 | 15 | 17-29 | 268 | 113 | 0.0488 |
| 116. | 269 | 170 | 122 | 15 | 15 | 17-29 | 270 | 113 | 0.0490 |
| 117. | 269 | 169 | 122 | 15 | 15 | 17-29 | 268 | 113 | 0.0492 |
| 118. | 270 | 167 | 122 | 15 | 15 | 17-29 | 269 | 111 | 0.0488 |
| Avg. | | | | | | | 269 | 112 | 0.049 |
| 119. | 300 | 205 | 121 | 21 | 21 | 27-57+ | 302 | 98 | 0.0387 |
| 120. | 299 | 209 | 121 | 21 | 21 | 27-57+ | 298 | 100 | 0.0396 |
| 121. | 291 | 205 | 126 | 21 | 21 | 27-57+ | 288 | 98 | 0.0404 |
| 122. | 296 | 205 | 127 | 21 | 21 | 27-57+ | 295 | 98 | 0.0401 |
| 123. | 291 | 207 | 127 | 21 | 21 | 27-57+ | 293 | 99 | 0.0401 |
| Avg. | | | | | | | 295 | 98 | 0.040 |
| 124. | 216 | 279 | 132 | 44 | 44 | 8-15 | 211 | 63 | 0.0271 |
| 125. | 220 | 279 | 132 | 44 | 44 | 8-15 | 215 | 63 | 0.0269 |
| 126. | 219 | 277 | 134 | 44 | 44 | 8-15 | 215 | 63 | 0.0269 |
| 127. | 219 | 279 | 134 | 44 | 44 | 8-15 | 218 | 63 | 0.0267 |
| 128. | 218 | 279 | 132 | 44 | 44 | 8-15 | 216 | 63 | 0.0266 |
| Avg. | | | | | | | 215 | 63 | 0.027 |
| 129. | 232 | 172 | 134 | 23 | 23 | 15-18 | 235 | 75 | 0.0348 |
| 130. | 233 | 176 | 132 | 23 | 23 | 15-18 | 235 | 77 | 0.0352 |
| 131. | 233 | 175 | 132 | 23 | 23 | 15-18 | 235 | 76 | 0.0350 |
| 132. | 229 | 175 | 134 | 23 | 23 | 15-18 | 231 | 76 | 0.0355 |
| 133. | 232 | 176 | 129 | 23 | 23 | 15-18 | 231 | 77 | 0.0352 |
| Avg. | | | | | | | 233 | 76 | 0.035 |
| 134. | 240 | 156 | 130 | 19 | 19 | 17-23 | 240 | 82 | 0.0390 |
| 135. | 241 | 156 | 130 | 19 | 19 | 17-23 | 238 | 82 | 0.0395 |
| 136. | 243 | 156 | 130 | 19 | 19 | 17-23 | 240 | 82 | 0.0394 |
| 137. | 238 | 152 | 133 | 19 | 19 | 17-23 | 239 | 80 | 0.0388 |
| 138. | 243 | 153 | 133 | 19 | 19 | 17-23 | 235 | 81 | 0.0402 |
| Avg. | | | | | | | 238 | 81 | 0.039 |
| 139. | 209 | 204 | 129 | 26 | 26 | 8-15 | 211 | 78 | 0.0350 |
| 140. | 211 | 205 | 129 | 26 | 26 | 8-15 | 208 | 79 | 0.0358 |
| 141. | 213 | 201 | 130 | 26 | 26 | 8-15 | 212 | 77 | 0.0351 |
| 142. | 213 | 199 | 129 | 26 | 26 | 8-15 | 215 | 77 | 0.0342 |
| 143. | 213 | 199 | 130 | 26 | 26 | 8-15 | 214 | 77 | 0.0345 |
| Avg. | | | | | | | 212 | 78 | 0.035 |
| 144. | 227 | 176 | 131 | 23 | 23 | 15-18 | 228 | 77 | 0.0354 |
| 145. | 227 | 174 | 132 | 23 | 23 | 15-18 | 228 | 76 | 0.0353 |
| 146. | 231 | 175 | 131 | 23 | 23 | 15-18 | 229 | 76 | 0.0355 |
| 147. | 230 | 172 | 132 | 23 | 23 | 15-18 | 227 | 75 | 0.0355 |
| 148. | 226 | 178 | 133 | 23 | 23 | 15-18 | 230 | 77 | 0.0355 |
| Avg. | | | | | | | 228 | 76 | 0.035 |
| 149. | 238 | 158 | 130 | 19 | 19 | 17-23 | 238 | 83 | 0.0394 |
| 150. | 237 | 158 | 131 | 19 | 19 | 17-23 | 236 | 83 | 0.0398 |
| 151. | 238 | 157 | 131 | 19 | 19 | 17-23 | 238 | 83 | 0.0394 |
| 152. | 239 | 158 | 132 | 19 | 19 | 17-23 | 238 | 83 | 0.0399 |
| 153. | 240 | 158 | 132 | 19 | 19 | 17-23 | 241 | 83 | 0.0395 |
| Avg. | | | | | | | 238 | 83 | 0.040 |
| 154. | 214 | 196 | 129 | 26 | 26 | 8-15 | 219 | 75 | 0.0333 |
| 155. | 215 | 196 | 128 | 26 | 26 | 8-15 | 218 | 75 | 0.0334 |

TABLE 6-continued

In-Bag Stack Height/Bag Utilization Factor Results for Sample Diaper Packages (Training Pants)

| Example | Height (mm) | Width (mm) | Depth (mm) | Bag Count | Pad Count Per Stack | Child Wt. Range (kg) | Folded Stack Length (mm) | In-Bag Stack Ht (mm) | Bag Utilization Factor (m²/pad/m) |
|---|---|---|---|---|---|---|---|---|---|
| 156. | 218 | 195 | 128 | 26 | 26 | 8-15 | 218 | 75 | 0.0337 |
| 157. | 215 | 196 | 129 | 26 | 26 | 8-15 | 218 | 75 | 0.0336 |
| 158. | 210 | 202 | 126 | 26 | 26 | 8-15 | 217 | 78 | 0.0334 |
| Avg. | | | | | | | 218 | 76 | 0.033 |
| 159. | 230 | 182 | 124 | 23 | 23 | 15-18 | 233 | 79 | 0.0347 |
| 160. | 230 | 182 | 128 | 23 | 23 | 15-18 | 232 | 79 | 0.0355 |
| 161. | 231 | 182 | 126 | 23 | 23 | 15-18 | 231 | 79 | 0.0354 |
| 162. | 226 | 170 | 131 | 23 | 23 | 15-18 | 233 | 74 | 0.0337 |
| 163. | 230 | 171 | 131 | 23 | 23 | 15-18 | 233 | 74 | 0.0343 |
| Avg. | | | | | | | 232 | 77 | 0.035 |
| 164. | 236 | 160 | 130 | 19 | 19 | 17-23 | 237 | 84 | 0.0396 |
| 165. | 235 | 161 | 131 | 19 | 19 | 17-23 | 236 | 85 | 0.0400 |
| 166. | 236 | 160 | 131 | 19 | 19 | 17-23 | 238 | 84 | 0.0396 |
| 167. | 235 | 160 | 135 | 19 | 19 | 17-23 | 240 | 84 | 0.0399 |
| 168. | 236 | 163 | 133 | 19 | 19 | 17-23 | 239 | 86 | 0.0403 |
| Avg. | | | | | | | 238 | 85 | 0.040 |
| 169. | 212 | 197 | 124 | 26 | 26 | 8-15 | 215 | 76 | 0.0311 |
| 170. | 213 | 190 | 123 | 26 | 26 | 8-15 | 215 | 73 | 0.0322 |
| 171. | 214 | 190 | 122 | 26 | 26 | 8-15 | 215 | 73 | 0.0322 |
| 172. | 211 | 194 | 127 | 26 | 26 | 8-15 | 215 | 75 | 0.0330 |
| 173. | 211 | 202 | 125 | 26 | 26 | 8-15 | 214 | 78 | 0.0339 |
| Avg. | | | | | | | 215 | 75 | 0.033 |
| 174. | 230 | 172 | 131 | 23 | 23 | 15-18 | 235 | 75 | 0.0341 |
| 175. | 232 | 173 | 131 | 23 | 23 | 15-18 | 233 | 75 | 0.0348 |
| 176. | 228 | 171 | 131 | 23 | 23 | 15-18 | 233 | 74 | 0.0341 |
| 177. | 226 | 172 | 132 | 23 | 23 | 15-18 | 235 | 75 | 0.0338 |
| 178. | 226 | 171 | 131 | 23 | 23 | 15-18 | 234 | 74 | 0.0337 |
| Avg. | | | | | | | 234 | 75 | 0.034 |
| 179. | 237 | 160 | 131 | 19 | 19 | 17-23 | 239 | 84 | 0.0396 |
| 180. | 235 | 161 | 131 | 19 | 19 | 17-23 | 240 | 85 | 0.0393 |
| 181. | 235 | 161 | 131 | 19 | 19 | 17-23 | 238 | 85 | 0.0397 |
| 182. | 233 | 154 | 132 | 19 | 19 | 17-23 | 239 | 81 | 0.0383 |
| 183. | 234 | 154 | 133 | 19 | 19 | 17-23 | 240 | 81 | 0.0384 |
| Avg. | | | | | | | 239 | 83 | 0.039 |
| 184. | 219 | 265 | 118 | 26 | 26 | 7-15 | 218 | 102 | 0.0406 |
| 185. | 216 | 265 | 120 | 26 | 26 | 7-15 | 220 | 102 | 0.0402 |
| 186. | 219 | 267 | 118 | 26 | 26 | 7-15 | 220 | 103 | 0.0405 |
| 187. | 220 | 269 | 120 | 26 | 26 | 7-15 | 220 | 103 | 0.0412 |
| 188. | 219 | 266 | 118 | 26 | 26 | 7-15 | 215 | 102 | 0.0413 |
| Avg. | | | | | | | 219 | 102 | 0.041 |
| 189. | 222 | 231 | 122 | 23 | 23 | 14-18 | 228 | 100 | 0.0406 |
| 190. | 224 | 229 | 119 | 23 | 23 | 14-18 | 225 | 100 | 0.0407 |
| 191. | 225 | 228 | 117 | 23 | 23 | 14-18 | 224 | 99 | 0.0405 |
| 192. | 225 | 228 | 117 | 23 | 23 | 14-18 | 228 | 99 | 0.0398 |
| 193. | 225 | 226 | 116 | 23 | 23 | 14-18 | 227 | 98 | 0.0395 |
| Avg. | | | | | | | 226 | 99 | 0.040 |
| 194. | 218 | 263 | 117 | 26 | 26 | 7-15 | 222 | 101 | 0.0394 |
| 195. | 219 | 265 | 116 | 26 | 26 | 7-15 | 224 | 102 | 0.0392 |
| 196. | 215 | 266 | 118 | 26 | 26 | 7-15 | 216 | 102 | 0.0406 |
| 197. | 217 | 267 | 116 | 26 | 26 | 7-15 | 220 | 103 | 0.0399 |
| 198. | 218 | 263 | 117 | 26 | 26 | 7-15 | 220 | 101 | 0.0397 |
| Avg. | | | | | | | 220 | 102 | 0.040 |
| 199. | 222 | 220 | 122 | 23 | 23 | 14-18 | 224 | 96 | 0.0399 |
| 200. | 225 | 220 | 122 | 23 | 23 | 14-18 | 228 | 96 | 0.0396 |
| 201. | 226 | 224 | 121 | 23 | 23 | 14-18 | 225 | 97 | 0.0406 |
| 202. | 228 | 228 | 121 | 23 | 23 | 14-18 | 224 | 99 | 0.0416 |
| 203. | 233 | 225 | 124 | 23 | 23 | 14-18 | 226 | 98 | 0.0420 |
| Avg. | | | | | | | 225 | 97 | 0.041 |
| 204. | 245 | 213 | 119 | 17 | 17 | 17-29 | 256 | 125 | 0.0490 |
| 205. | 247 | 212 | 120 | 17 | 17 | 17-29 | 255 | 125 | 0.0496 |
| 206. | 245 | 214 | 118 | 17 | 17 | 17-29 | 255 | 126 | 0.0492 |
| 207. | 248 | 212 | 119 | 17 | 17 | 17-29 | 252 | 125 | 0.0501 |
| 208. | 241 | 215 | 119 | 17 | 17 | 17-29 | 247 | 126 | 0.0505 |
| Avg. | | | | | | | 253 | 125 | 0.050 |
| 209. | 260 | 171 | 119 | 13 | 13 | 26-39 | 265 | 132 | 0.0556 |
| 210. | 258 | 171 | 121 | 13 | 13 | 26-39 | 263 | 132 | 0.0562 |
| 211. | 249 | 170 | 120 | 13 | 13 | 26-39 | 252 | 131 | 0.0565 |
| 212. | 249 | 171 | 120 | 13 | 13 | 26-39 | 255 | 132 | 0.0561 |
| 213. | 249 | 171 | 118 | 13 | 13 | 26-39 | 254 | 132 | 0.0558 |
| Avg. | | | | | | | 258 | 131 | 0.056 |
| 214. | 248 | 216 | 118 | 17 | 17 | 17-29 | 256 | 127 | 0.0498 |
| 215. | 244 | 214 | 119 | 17 | 17 | 17-29 | 253 | 126 | 0.0496 |
| 216. | 250 | 212 | 118 | 17 | 17 | 17-29 | 255 | 125 | 0.0496 |

TABLE 6-continued

In-Bag Stack Height/Bag Utilization Factor Results for Sample Diaper Packages (Training Pants)

| Example | Height (mm) | Width (mm) | Depth (mm) | Bag Count | Pad Count Per Stack | Child Wt. Range (kg) | Folded Stack Length (mm) | In-Bag Stack Ht (mm) | Bag Utilization Factor ($m^2$/pad/m) |
|---|---|---|---|---|---|---|---|---|---|
| 217. | 245 | 213 | 120 | 17 | 17 | 17-29 | 247 | 125 | 0.0510 |
| 218. | 245 | 214 | 121 | 17 | 17 | 17-29 | 245 | 126 | 0.0518 |
| Avg. | | | | | | | 251 | 126 | 0.050 |

Examples 104-108 are commercially available airfelt training pants sold by Kimberly-Clark Corporation under the trademark HUGGIES GOOD NITES (girl S-M; bag count 27; Lot #'s PA19915B 23:25—Ex. 104, 105 and 108; PA916113X 17:29—Ex. 106; and PA916113X 17:31—Ex. 107).

Examples 109-113 are commercially available airfelt training pants sold by Kimberly-Clark Corporation under the trademark HUGGIES GOOD NITES (girl L-XL; bag count 21; Lot #'s PA920414F 17:46—Ex. 109 and 110; PA915614B 01:54; PA915414F 10:38; and PA915614B 01:52).

Examples 114-118 are commercially available airfelt training pants sold by Kimberly-Clark Corporation under the trademark HUGGIES GOOD NITES (boy S-M; bag count 15; Lot #'s PA917215F 15:09; PA917915F 16:02; PA917915F 16:04; PA916315F 10:44; and PA917915F 16:04, respectively).

Examples 119-123 are commercially available airfelt training pants sold by Kimberly-Clark Corporation under the trademark HUGGIES GOOD NITES (boy L-XL; bag count 21; Lot #'s PA919613F 14:33—Ex. 119 and 120; and PA920914F 18:05—Ex. 121-123).

Examples 124-128 are commercially available airfelt training pants sold by Kimberly-Clark Corporation under the trademark HUGGIES LEARNING DESIGN (girl 2T/3T; bag count 44; Lot #'s PA920017F 07:03; PA920910B 03:55; PA919917B 06:28; and PA920910B 04:17-Ex. 127 and 128, respectively). These particular examples do not have a substantially cellulose free absorbent core as defined herein.

Examples 129-133 are commercially available airfelt training pants sold by Kimberly-Clark Corporation under the trademark HUGGIES LEARNING DESIGN (girl 3T/4T; bag count 23; Lot #'s BI919619B 20:40; BI917919B 05:35—Ex. 130-132; and PA917009X 19:14, respectively). These particular examples do not have a substantially cellulose free absorbent core as defined herein.

Examples 134-138 are commercially available airfelt training pants sold by Kimberly-Clark Corporation under the trademark HUGGIES LEARNING DESIGN (girl 4T/5T; bag count 19; Lot # PA921018F 10:48). These particular examples do not have a substantially cellulose free absorbent core as defined herein.

Examples 139-143 are commercially available airfelt training pants sold by Kimberly-Clark Corporation under the trademark HUGGIES LEARNING DESIGN (boy 2T/3T; bag count 26; Lot #'s PA922610F08:48—Ex. 139 and 140; PA921210B23:28; PA92120B23:21; and PA92120B23:20). These particular examples do not have a substantially cellulose free absorbent core as defined herein.

Examples 144-148 are commercially available airfelt training pants sold by Kimberly-Clark Corporation under the trademark HUGGIES LEARNING DESIGN (boy 3T/4T; bag count 23; Lot #'s PA92189B02:00—Ex. 144-147 and PA919312B03:07). These particular examples do not have a substantially cellulose free absorbent core as defined herein.

Examples 149-153 are commercially available airfelt training pants sold by Kimberly-Clark Corporation under the trademark HUGGIES LEARNING DESIGN (boy 4T/5T; bag count 19; Lot #'s PA920718F 12:39; and PA915818X 03:06). These particular examples do not have a substantially cellulose free absorbent core as defined herein.

Examples 154-158 are commercially available airfelt training pants sold by Kimberly-Clark Corporation under the trademark HUGGIES COOL ALERT (girl 2T/3T; bag count 26; Lot #'s PA914610X 01:46—Ex. 154-157; and UT911011F 09:25). These particular examples do not have a substantially cellulose free absorbent core as defined herein.

Examples 159-163 are commercially available airfelt training pants sold by Kimberly-Clark Corporation under the trademark HUGGIES COOL ALERT (girl 3T/4T; bag count 23; Lot #'s UT911812B 23:34—Ex. 159 and 160; UT919412F07:36—Ex. 161; and BI917219B 03:11—Ex. 162 and 163). These particular examples do not have a substantially cellulose free absorbent core as defined herein.

Examples 164-168 are commercially available airfelt training pants sold by Kimberly-Clark Corporation under the trademark HUGGIES COOL ALERT (girl 4T/5T; bag count 19; Lot #'s UT909610B 23:35—Ex. 164-166; and BI912818F 08:46—Ex. 167 and 168). These particular examples do not have a substantially cellulose free absorbent core as defined herein.

Examples 169-173 are commercially available airfelt training pants sold by Kimberly-Clark Corporation under the trademark HUGGIES COOL ALERT (boy 2T/3T; bag count 26; Lot #'s WP919510E—Ex. 169-172; and PA914810X 18:23). These particular examples do not have a substantially cellulose free absorbent core as defined herein.

Examples 174-178 are commercially available airfelt training pants sold by Kimberly-Clark Corporation under the trademark HUGGIES COOL ALERT (boy 3T/4T; bag count 23; Lot #'s UT917312B 21:51—Ex. 174 and 175; UT917312B 17:43—Ex. 176 and 177; and UT917312F 17:42). These particular examples do not have a substantially cellulose free absorbent core as defined herein.

Examples 179-183 are commercially available airfelt training pants sold by Kimberly-Clark Corporation under the trademark HUGGIES COOL ALERT (boy 4T/5T; bag count 19; Lot #'s BI910818B 23:42—Ex. 179 and 180; PA911418X 02:48—Ex. 181; and BI919918B 01:34—Ex. 182 and 183). These particular examples do not have a substantially cellulose free absorbent core as defined herein.

Examples 184-188 are commercially available airfelt training pants sold by The Procter & Gamble Company under the trademark PAMPERS EASY UPS (girl size 4; bag count 26; Lot #'s 9215U0175512:45; 9214U0175516:19—Ex. 185-187; and 9214U175512:46).

Examples 189-193 are commercially available airfelt training pants sold by The Procter & Gamble Company under the trademark PAMPERS EASY UPS (girl size 5; bag count 23; Lot #'s 914U0112806:15; 9205U0175520:33; and 918U0175517:44—Ex. 191-193).

Examples 194-198 are commercially available airfelt training pants sold by The Procter & Gamble Company under the trademark PAMPERS EASY UPS (boy size 4; bag count 26; Lot #'s 9109U01701R06:26—Ex. 194 and 195; 9191U0175503:59—Ex. 196 and 197; and 9109U1701R06:25).

Examples 199-203 are commercially available airfelt training pants sold by The Procter & Gamble Company under the trademark PAMPERS EASY UPS (boy size 5; bag count 23; Lot #'s 9227U0175510:51—Ex. 199 and 200; 9123U0175504:27; 9207U175519:34; and 9207U0175519:30).

Examples 204-208 are commercially available airfelt training pants sold by The Procter & Gamble Company under the trademark PAMPERS UNDERJAMS (girl size S/M; bag count 17; Lot #'s 9213U0112601:47—Ex. 204-207; and 9156U0112600:34).

Examples 209-213 are commercially available airfelt training pants sold by The Procter & Gamble Company under the trademark PAMPERS UNDERJAMS (girl size L/XL; bag count 13; Lot #'s 9030U0112620:06; 9030U0112616:52; and 9136U0112600:40—Ex. 211-213).

Examples 214-218 are commercially available airfelt training pants sold by The Procter & Gamble Company under the trademark PAMPERS UNDERJAMS (boy size S/M; bag count 17; Lot #'s 9091U0112623:43; 9147U0112621:33; 9212U0112618L54; and 9220U0112603:23—Ex. 217 and 218).

Test Methods

The test methods and apparatus described below may be useful in testing embodiments of the present disclosure:

Stiffness Test

The Stiffness Test is described in detail above.

In-Bag Stack Height

The In-Bag Stack Height is determined as follows:

Equipment

Universal Diaper Packaging Tester (UDPT) (Model # M-ROEL; Machine # MK-1071), including a horizontal sliding plate (horizontal plate that moves up and down in a vertical plane) for adding weights. It is counter-balanced by a suspended weight to assure that no downward force is added from the horizontal sliding plate assembly to the diaper package at all times. The UDPT is available from Matsushita Industry Co. LTD, 7-21-101, Midorigaoka-cho, Ashiya-city, Hyogo JAPAN. Zip code: 659-0014.

A 850 g (±5 g) weight.

Definitions

As illustrated in FIG. 5a, package width 108 is defined as the maximum distance between the two highest bulging points along the same compression stack axis 110 of a diaper package.

In-Bag Stack Height=(Package Width/Pad Count Per Stack)×10 pads of diapers.

Apparatus Calibration

Pull down the horizontal sliding plate until its bottom touches the tester base plate.

Set the digital meter located at the side of the horizontal sliding scale to zero mark.

Raise the horizontal sliding plate away from the tester base plate.

Test Procedure

Put one of the side panel of the diaper package along its width standing at the center of the tester base plate. Make sure the vertical sliding plate (vertical plate that moves left and right in a horizontal plane) is pulled to the right so it does not touch the package being tested.

Add the 850 g weight onto the vertical sliding plate.

Allow the horizontal sliding plate to slide down slowly until its bottom lightly touches desired highest point of the package.

Measure the package width in mm (distance from the top of the base plate to the top of the diaper package). Record the reading that appears on the digital meter.

Remove the 850 g weight.

Raise the horizontal sliding plate away from the diaper package.

Remove the diaper package.

Calculation/Reporting

Calculate and report the "In-Bag Stack Height"=(Package Width/Pad Count Per Stack)×10.

Report Sample Identification, i.e. complete description of product being tested (product brand name/size).

Report the determined value for each width measurement to the nearest 1 mm.

At least five diaper packages having the same pad count are measured in this manner for a given product and the in-bag stack height values are aggregated to calculate an average and standard deviation.

Report the Production Date of the measured package (taken from package coding).

Report the Testing Date and Analytical Method used.

Folded Stack Length

The Folded Stack Length is determined as follows:

Equipment

Universal Diaper Packaging Tester (UDPT) (Model # M-ROEL; Machine # MK-1071), including a horizontal sliding plate (horizontal plate that moves up and down in a vertical plane) for adding weights. It is counter-balanced by a suspended weight to assure that no downward force is added from the horizontal sliding plate assembly to the diaper package at all times. The UDPT is available from Matsushita Industry Co. LTD, 7-21-101, Midorigaoka-cho, Ashiya-city, Hyogo JAPAN. Zip code: 659-0014.

A 850 g (±5 g) weight.

Definitions

As illustrated in FIGS. 7a and 7b, pad nose 142 is the outer pad folding of an absorbent article and pad tail 140 is the outer endflap end of an absorbent article.

As further illustrated in FIGS. 7a and 7b, stack length is the average folded pad length 144 of 10 pads of diapers.

Apparatus Calibration

Raise the horizontal sliding plate away from the tester base plate to allow stacks of diapers to be placed on the tester base plate.

Move the vertical sliding plate (vertical plate that moves left and right in a horizontal plane) to the left until it touches the vertical anchored plate.

Set the digital meter located on the side of the horizontal sliding plate to the zero mark.

Move the vertical sliding plate to the right to allow stacks of diapers to be placed on the tester base plate.

Stack Length

Preparation

Place 10 diapers individually on top of each other on the tester base. For taped diapers, the landing zone side is upwards within the UDPT. For pants, the front-side is upwards within the UDPT.

Place the stack of 10 diapers along the folded pad length ("nose" facing vertical anchored plate) on the tester base, such that good contact is achieved between the stack and the vertical anchored plate.

Test Procedure

Add the 850 g weight onto the horizontal sliding plate.

Allow the horizontal sliding plate to slide down slowly until its bottom lightly touches the stack of diapers. Release the plate such that the plate comes to rest on the diaper stack.

Condition the stack under the weight for 15 seconds.

Move the vertical sliding plate towards the anchored vertical plate until the plate touches the tail of the first pad. Stop moving the vertical plate as soon as it gets in contact with the tail of the first pad.

Record the reading that appears on the digital meter.

Remove the 850 g weight.

Raise the horizontal sliding plate away from the stack of diapers.

Remove the stack of diapers.

Calculation/Reporting

Report the determined value for stack length. At least five samples (5 diaper packages having the same pad count) are measured in this manner for a given product and the folded stack length values are aggregated to calculate an average and standard deviation.

Report Sample Identification, i.e. complete description of product being tested (product brand name/size).

Report the Production Date of the measured package (taken from package coding).

Report the Testing Date and Analytical Method used.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A pallet of absorbent products comprising:
a plurality of packages, each having a plurality of disposable absorbent articles disposed within the interior space of the package, each of the disposable absorbent articles having a topsheet, a backsheet, a substantially cellulose free absorbent core located between the topsheet and the backsheet, a first waist region, a second waist region, a crotch region extending longitudinally between the first and second waist regions, and a fastening member extending laterally outward from the second waist region and adapted to releasably connect with a landing zone located in the first waist region;
wherein the plurality of packages are arranged on the pallet such that the density of the plurality of packages on the pallet exhibit a density of from 11.0 lbs/ft$^3$ to 14.6 lbs/ft$^3$.

2. The pallet according to claim 1, wherein the density is from 11.2 lbs/ft$^3$ to 13.9 lbs/ft$^3$.

3. The pallet according to claim 1, wherein the density is from 11.8 lbs/ft$^3$ to 12.0 lbs/ft$^3$.

4. The pallet according to claim 1, wherein the pallet's maximum load capacity, excluding the weight of the pallet itself, is 765 lbs.

5. The pallet according to claim 1, wherein the pallet's length is about 48 inches and its width is about 40 inches.

6. The pallet according to claim 1, wherein the pallet's height is about 5.75 inches.

7. The pallet according to claim 1, wherein the height of pallet and plurality of packages arranged on the pallet is 48 inches or less.

8. The pallet according to claim 1, wherein the absorbent articles are packaged in a plurality of packages such that the absorbent articles have an In-Bag Stack Height of less than or equal to about 80 mm according to the In-Back Stack Height Method described herein.

9. The pallet according to claim 1, wherein the absorbent articles are packaged in a plurality of packages such that the absorbent articles have an In-Bag Stack Height from about 72 mm to about 80 mm according to the In-Back Stack Height Method described herein.

10. The pallet according to claim 1, wherein the absorbent articles are packaged in a plurality of packages such that the absorbent articles have an In-Bag Compression of greater than or equal to about 58% according to In-Bag Compression equation as defined herein.

11. The pallet according to claim 1, wherein the absorbent articles are packaged in a plurality of packages such that the absorbent articles have an In-Bag Compression from about 58% to about 62% according to In-Bag Compression equation as defined herein.

12. The pallet according to claim 1, wherein at least one of the absorbent articles have a longitudinal bending stiffness of less than or equal to about 355 N/m according to the Stiffness Test described herein.

13. The pallet according to claim 1, wherein at least one of the absorbent articles have a longitudinal bending stiffness from about 285 N/m to about 355 N/m according to the Stiffness Test described herein.

14. The pallet according to claim 1, wherein the absorbent articles are packaged in a plurality of packages such that the absorbent articles have a Bag Utilization Factor of less than or equal to about 0.030 m$^2$/pad/m according to Bag Utilization Factor equation described herein.

15. The pallet according to claim 1, wherein the absorbent articles are packaged in a plurality of packages such that the absorbent articles have a Bag Utilization Factor from about 0.027 m$^2$/pad/m to about 0.030 m$^2$/pad/m according to Bag Utilization Factor equation described herein.

16. The pallet according to claim 1, wherein the absorbent articles are selected from the group consisting of diapers, training pants, and adult incontinence undergarments.

17. The pallet according to claim 16, wherein the absorbent articles are diapers.

18. A pallet of absorbent products comprising:
- a plurality of packages, each having a plurality of disposable diapers disposed within the interior space of the package, each of the disposable diapers having a topsheet, a backsheet, a substantially cellulose free absorbent core located between the topsheet and the backsheet, a first waist region, a second waist region, a crotch region extending longitudinally between the first and second waist regions, and a fastening member extending laterally outward from the second waist region and adapted to releasably connect with a landing zone located in the first waist region;
- wherein the plurality of packages are arranged on the pallet such that the density of the plurality of packages on the pallet exhibit a density of from 11.2 lbs/ft$^3$ to 13.9 lbs/ft$^3$;
  - wherein the pallet's length is about 48 inches, its width is about 40 inches, and its height is about 5.75 inches; and
  - wherein the height of pallet and plurality of packages arranged on the pallet is about 48 inches or less.

19. A shipping optimization process for absorbent articles comprising the steps of:
- (a) identifying a plurality of pallets on which the absorbent articles are to be shipped;
- (b) identifying a semi-trailer in which the pallets are to be shipped; and
- (c) loading the plurality of pallets into the semi-trailer;

wherein the plurality of pallets of absorbent articles comprise a plurality of packages, each having a plurality of disposable absorbent articles disposed within the interior space of the package, each of the disposable absorbent articles having a topsheet, a backsheet, a substantially cellulose free absorbent core located between the topsheet and the backsheet, a first waist region, a second waist region, a crotch region extending longitudinally between the first and second waist regions, and a fastening member extending laterally outward from the second waist region and adapted to releasably connect with a landing zone located in the first waist region; and wherein the plurality of packages are arranged on the pallet such that the density of the plurality of packages on the pallet exhibit a density of from about 11.0 lbs/ft$^2$ to about 14.6 lbs/ft$^2$.

20. The process according to claim 19, wherein step (c) comprises loading about 60 pallets into the semi-trailer.

21. The process according to claim 19, wherein the absorbent articles are selected from the group consisting of diapers, training pants, and adult incontinence undergarments.

22. The process according to claim 21, wherein the absorbent articles are diapers.

23. The process according to claim 19, wherein the pallet's length is about 48 inches and its width is about 40 inches.

24. The process according to claim 19, wherein the pallet's height is about 5.75 inches.

25. The process according to claim 19, wherein the height of pallet and plurality of packages arranged on the pallet is about 48 inches or less.

* * * * *